US010790045B1

(12) United States Patent
Goyal et al.

(10) Patent No.: US 10,790,045 B1
(45) Date of Patent: Sep. 29, 2020

(54) SYSTEM AND METHOD FOR SCREENING HOMOPOLYMERS, COPOLYMERS OR BLENDS FOR FABRICATION

(71) Applicant: Corning Incorporated, Corning, NY (US)

(72) Inventors: Sushmit Sunil Kumar Goyal, Painted Post, NY (US); Franklin Langlang Lee, Painted Post, NY (US); Adama Tandia, Nelson, PA (US); Mardochee Reveil, Ithaca, NY (US)

(73) Assignee: Corning Incorporated, Corning, NY (US)

(*) Notice: Subject to any disclaimer, the term of this patent is extended or adjusted under 35 U.S.C. 154(b) by 0 days.

(21) Appl. No.: 16/653,310

(22) Filed: Oct. 15, 2019

Related U.S. Application Data

(60) Provisional application No. 62/908,054, filed on Sep. 30, 2019.

(51) Int. Cl.
*G01N 33/48* (2006.01)
*G01N 33/50* (2006.01)
(Continued)

(52) U.S. Cl.
CPC ............ *G16C 20/20* (2019.02); *G06N 3/126* (2013.01); *G16C 20/10* (2019.02); *G16C 20/40* (2019.02); *G16C 20/70* (2019.02)

(58) Field of Classification Search
None
See application file for complete search history.

(56) References Cited

U.S. PATENT DOCUMENTS

| 5,302,896 A | 4/1994 | Dechene et al. |
| 6,208,942 B1 | 3/2001 | Hurst et al. |
(Continued)

FOREIGN PATENT DOCUMENTS

| KR | 827744 B1 | 5/2008 |
| KR | 2016127486 A | 11/2016 |

OTHER PUBLICATIONS

Southern et al. Analyzing and comparing nucleic acid sequences by hybridization to arrays of oligonucleotides: Evaluation using experimental models. Genomics, vol. 13, pp. 1008-1017. (Year: 1992).*

(Continued)

*Primary Examiner* — Russell S Negin

(57) ABSTRACT

Techniques for screening homopolymers, copolymers or blends for fabrication are disclosed. A data repository stores data points. Each data point comprises a structural repeating unit (SRU) and at least one material property value for the SRU. Each SRU is a homopolymer SRU, a copolymer component SRU or a blend component SRU. A machine determines a fingerprint for at least a subset of the SRUs in the data repository. The machine stores, in the data repository, each determined fingerprint in conjunction with a corresponding SRU. The machine generates a quantitative modeling engine to predict material property values, based on SRUs, for homopolymers, copolymers or blends. The quantitative modeling engine is based, at least in part, on the fingerprints. The machine identifies, using the quantitative modeling engine, at least one homopolymer SRU, copolymer SRU set or blend SRU set that has a material property value within a given range.

13 Claims, 19 Drawing Sheets

(51) Int. Cl.
*G16C 20/20* (2019.01)
*G16C 20/70* (2019.01)
*G06N 3/12* (2006.01)
*G16C 20/40* (2019.01)
*G16C 20/10* (2019.01)

(56) References Cited

U.S. PATENT DOCUMENTS

| | | | |
|---|---|---|---|
| 8,862,438 | B2 | 10/2014 | Drabish et al. |
| 9,757,706 | B2 | 9/2017 | Cronin |
| 2003/0069698 | A1 | 4/2003 | Uchiyama et al. |
| 2004/0161785 | A1 | 8/2004 | Cawse et al. |
| 2010/0010955 | A1 | 1/2010 | Deshpande |
| 2015/0133306 | A1* | 5/2015 | Cronin ............... B01J 19/0046 506/1 |

OTHER PUBLICATIONS

Bicerano; "Prediction of Polymer Properties" ; Third Edition, Revised and Expanded; Marcel Dekker, Inc.; pp. 22-49, 566-570 and 570-573; 2009.

Brown et al; "A Graph-Based Genetic Algorithm and its Applicatio to the Multiobjective Evolution of Median Molecules" ; Journal of Chemical Information and Computer Sciences; (2004), 44, 10791087.

Jensen; "Graph-Based Genetic Algorithm and Generative Model/ Monte Carlo Tree Search for the Exploration of Chemical Space" ; 2018; Chemrxiv. Preprint; https://doi.org/10.26434/chemrxiv.7240751. v2; 9 Pages.

Mannodi-Kanakkithodi et al; "Scoping the Polymer Genome: A Roadmap for Rational Polymer Dielectrics Design and Beyong" ; Materials Today; 2018, 12 Pages.

Schneider et al; "Coping With Complexity in Ligand-Based De Novo Design" ; American Chemical Society; Frontiers in Molecular Design and Chemical Informaiton Science—Herman Skolnik Award Symposium 2015: Jurgen Bajorath; (2016); pp. 143-158.

Segler et al; "Generating Focused Molecule Libraries for Drug Discovery With Recurrent Neural Networks" ; ACS Central Science 2018, 4, 120131.

Sumita et al; "Hunting for Organic Molecules With Artifical Intelligence: Molecules Optimized for Desired Excitation Energies" ; ACS Central Science 2018, 4, 11261133.

Virshup et al; "Stochastic Voyages into Uncharted Chemical Space Produce a Representative Library of All Possible Drug-Like Compounds" ; Journal of the American Chemical Society, 2013, 135, 72967303.

Wu et al; "Machine-Learning-Assisted Discovery of Polymers With High Thermal Conductivity Using a Molecular Design Algorithm" ; Nature, Computational Materials; 2019; 11 Pages.

Yang et al; "CHEMTS: An Efficient Python Library for De Novo Molecular Generation" ; Science and Technology of Advanced Materials 2017, 18, 972976.

Krizhevsky et al; "Imagenet Classification With Deep Convolutional Neural Networks," Part of "Advances in Neural Information Processing Systems 25" (NIPS 2012), Available at: papers.nips.cc/paper/4824-imagenet-classification-with-deep-convolutional-neural-networ, last visited Aug. 28, 2019; 9 Pages.

\* cited by examiner

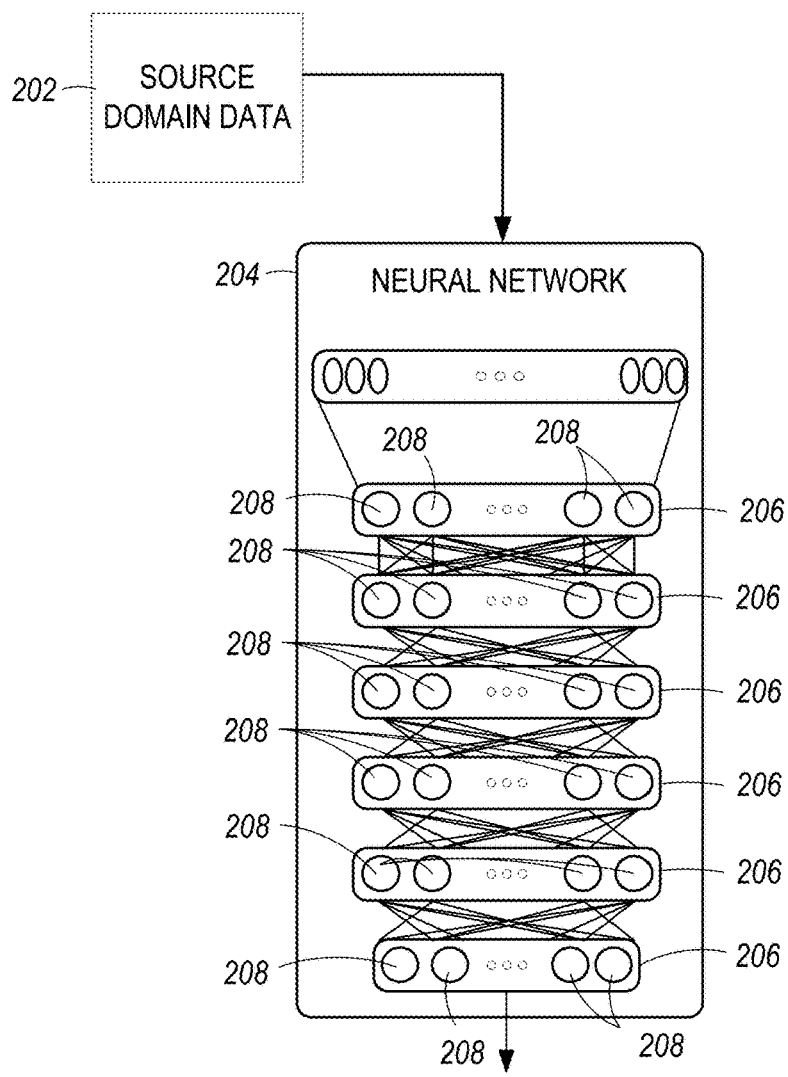
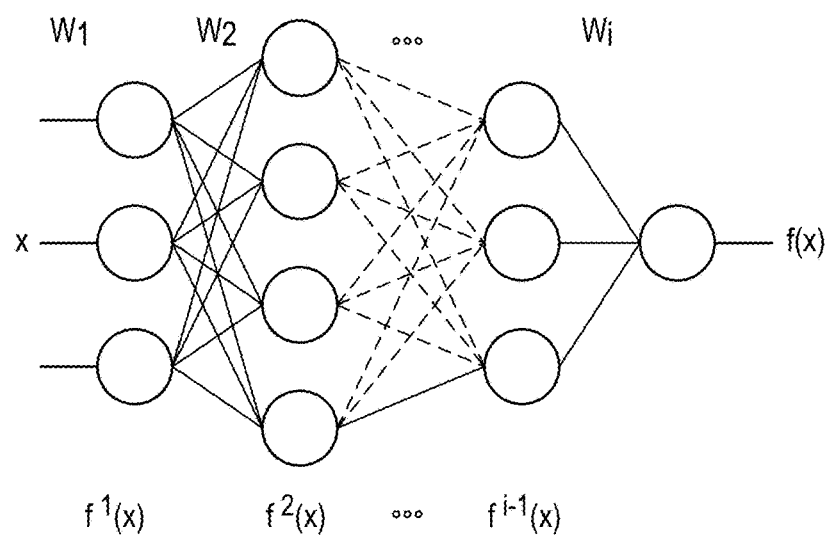
FIG. 2

| HOME | ABOUT | CALC | SCREEN | PLOT | LOG |

PREDICTION INPUT

INPUT AREA

SPECIFY TYPE OF CALCULATION:
- ○ HOMOPOLYMER CALCULATION
- ◉ COPOLYMER CALCULATION
- ○ COPOLYMER OPTIMIZATION

SPECIFY PROPERTIES:
☑ REFRACTIVE INDEX ☑ DENSITY
☑ COHESIVE ENERGY DENSITY ☑ SOLUBILITY PARAMETER ☑ SURFACE TENSION

ENTER SMILES OF THE POLYMER SRUS:

SMILES 1: `*C(C)C(C(=O)OC)C*`
SMILES 2: `*C(C)C(C(=O)OC)C*`

ENTER FRACTION OF SRU 1 WITHIN THE COPOLYMER:
`0.5`

SELECT FRACTION TYPE:  MASS FRACTION    MOLE FRACTION

[SUBMIT]

EXAMPLES

COPY AND PASTE THESE SMILES STRINGS INTO THE BOX AND SUBMIT TO TRY IT OUT!

DRAW YOUR OWN SRU

SMILES: `*CC(*)c1cccc1`
[CLOSE]

1. DRAW THE SRU, USING * ATOMS TO REPRESENT THE HEAD AND TAIL ATOMS (CLICK ON THE X AND TYPE IN * AS THE ATOMIC SMILES)
2. CLICK THE SMILEY FACE ICON AT THE TOP LEFT
3. COPY AND PASTE THE RESULTING SMILES STRING INTO THE BOX AND SUBMIT

BINARY CALCULATION RESULT

INPUT SMILES: *C(C)(C(-O)OC)C* *CC(*)ClCCCCC1
INPUT FRACTION OF SRU 1: 0.5 (MASS FRACTION)
PROPERTIES OF INTEREST: REFRACTIVE INDEX, DENSITY, COHESIVE ENERGY DENSITY, SOLUBILITY PARAMETER, SURFACE TENSION

PREDICTED REFRACTIVE INDEX (EMPIRICAL): 1.5470
*NOTE: NONLINEAR INTERPOLATION*
PREDICTED DENSITY (EMPIRICAL): 1.115 G/CC
*NOTE: NONLINEAR INTERPOLATION*
PREDICTED COHESIVE ENERGY DENSITY (EMPIRICAL): 31.87 KJ/MOL
*NOTE: LINEAR INTERPOLATION*
PREDICTED SOLUBILITY PARAMETER (EMPIRICAL): 18.65 SQRT(J/CC)
*NOTE: NONLINEAR INTERPOLATION*
PREDICTED SURFACE TENSION (EMPIRICAL): 37.10 DYN/CM
*NOTE: NONLINEAR INTERPOLATION*

FIG. 11A

BINARY OPTIMIZATION RESULT

INPUT SMILES: *C(C)(C)C(=O)OC)C**CC(*)ClCCCC1
PROPERTIES OF INTEREST: REFRACTIVE INDEX, SURFACE TENSION
TARGET VALUES: 1.547, 37.1

PREDICTED FRACTIONS (EMPIRICAL): F1 = 0.500, F2 = 0.500 (MASS FRACTION)

OPTIMIZED REFRACTIVE INDEX (EMPIRICAL): 1.5469
*NOTE: NONLINEAR INTERPOLATION*
OPTIMIZED SURFACE TENSION (EMPIRICAL): 37.10 DYN/CM
*NOTE: NONLINEAR INTERPOLATION*

BACK TO INPUT

BINARY OPTIMIZATION RESULT

INPUT SMILES: *C(CL)(CL)C(*)(CL)CLC(CL)C(CL)C(CL)C(CL)C1C1, O=C(OF)C(F)(*)C*
PROPERTIES OF INTEREST: REFRACTIVE INDEX
TARGET VALUES: 1.440

PREDICTED FRACTIONS (EMPIRICAL): FL = 0.123, F2 = 0.877 (MASS FRACTION)

OPTIMIZED REFRACTIVE INDEX (EMPIRICAL): 1.4400
*NOTE: NONLINEAR INTERPOLATION*

BACK TO INPUT

SYSTEM AND METHOD FOR SCREENING HOMOPOLYMERS, COPOLYMERS OR BLENDS FOR FABRICATION

This application claims the benefit of priority under 35 U.S.C. § 119 of U.S. Provisional Application Ser. No. 62/908,054, filed on Sep. 30, 2019, the content of which is relied upon and incorporated herein by reference in its entirety.

TECHNICAL FIELD

Embodiments pertain to polymer science. Some embodiments relate to homopolymers, copolymers, and blends. Some embodiments relate to systems and methods for screening homopolymers, copolymers or blends for fabrication.

BACKGROUND

Polymers are important components of many products. The choice of which polymer to incorporate in each product (or for each use case) may depend on property constraints. Finding the ideal polymer for each application might require months of synthesis, acquisition, fabrication, and characterization. The candidate polymers that are tested are based mainly on scientists' experience and intuition, and only a few are typically tested in parallel.

BRIEF DESCRIPTION OF THE DRAWINGS

FIG. 2 illustrates an example neural network, in accordance with some embodiments.

FIGS. 10A-10B illustrate an example user interface for a calculation capability, in accordance with some embodiments.

FIGS. 11A-11B illustrate an example user interface for an optimization capability, in accordance with some embodiments.

FIGS. 12A-12B illustrate an example user interface for a screening capability, in accordance with some embodiments.

SUMMARY

Figure 1:
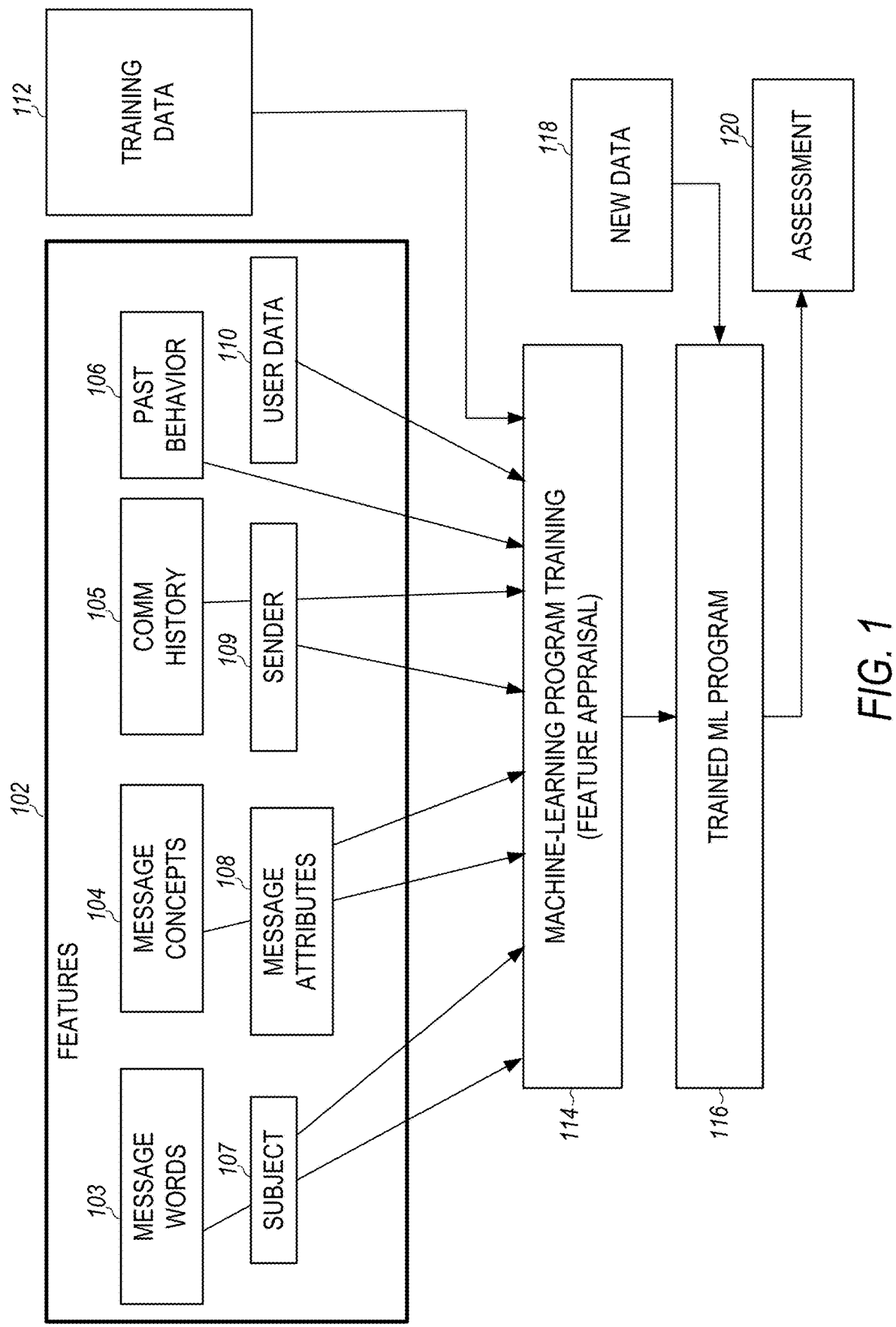
FIG. 1 illustrates the training and use of a machine-learning program, in accordance with some embodiments.

The present disclosure generally relates to screening homopolymers, copolymers or blends for fabrication.

According to some aspects of the technology described herein, a method comprises storing, in a data repository, a plurality of data points, each data point comprising a structural repeating unit (SRU) and at least one material property value for the SRU, wherein each SRU is a homopolymer SRU, a copolymer component SRU or a blend component SRU. The method comprises determining, using a computing machine, a fingerprint for at least a subset of the SRUs in the data repository. The method comprises storing, in the data repository, each determined fingerprint in conjunction with a corresponding SRU. The method comprises generating, using at least a subset of the plurality of data points in the data repository, a quantitative modeling engine to predict material property values, based on SRUs, for homopolymers, copolymers or blends, wherein the quantitative modeling engine is based, at least in part, on the fingerprints. The method comprises identifying, using the quantitative modeling engine, at least one homopolymer SRU, copolymer SRU set or blend SRU set that has a material property value within a given range, wherein the at least one homopolymer SRU, copolymer component SRU or blend component SRU is selected from a set of SRUs that is different from the SRUs represented by the plurality of data points in the data repository. The method comprises providing an output representing the identified at least one homopolymer SRU, copolymer SRU set or blend SRU set.

Other aspects include a machine-readable medium storing instructions to perform one or more of the above methods and a system comprising processing circuitry and memory, the memory storing instructions which, when executed by the processing circuitry, cause the processing circuitry to perform one or more of the above methods.

DETAILED DESCRIPTION

The following description and the drawings sufficiently illustrate specific embodiments to enable those skilled in the art to practice them. Other embodiments may incorporate structural, logical, electrical, process, and other changes. Portions and features of some embodiments may be included in, or substituted for, those of other embodiments. Embodiments set forth in the claims encompass all available equivalents of those claims.

As discussed above, homopolymers, copolymers and blends are important components of many products. The choice of which homopolymer, copolymer or blend to incorporate in each product (or for each use case) may depend on property constraints. Finding the ideal homopolymer, copolymer or blend for each application might require months of synthesis, acquisition, fabrication, and characterization. The candidate homopolymers, copolymers or blends that are tested are based mainly on scientists' experience and intuition, and only a few are typically tested in parallel.

Computational techniques have been used to overcome some challenges of the purely experimental approach. For example, atomistic simulation techniques can probe electronic structure or chain dynamics of polymers to calculate a set of properties for a polymer system. These approaches, however, might have high computational cost, as they typically include fine-grained physical detail.

Polymers are the macromolecules formed by linking of a large number of small units called monomers through chemical reactions. The process of formation of polymers is called polymerization. The chemical and physical properties of a polymer mainly depend on the type of monomer or monomers used to form the polymer. Based on the number of different types of monomers used to form a polymer molecule, there are two types of polymers: homopolymers and copolymers. One difference between homopolymer and copolymer is that homopolymers are produced by using a single type of monomer, whereas copolymers are formed by using two different types of monomers. Some differences between homopolymers and copolymer are illustrated in Table 1. As used herein, the term "polymer blend" encompasses its plain and ordinary meaning. A polymer blend may include a mixture of two or more polymers that have been blended together to create a new material with different physical properties.

TABLE 1

Homopolymer versus copolymer.

| Homopolymer | Copolymer |
| --- | --- |
| Homopolymers may be formed through addition polymerization, among other formation techniques. | Copolymers may be formed through condensation polymerization, among other formation techniques. |
| Include single species of repeating units | Include two or more types of repeating units |
| Have a single type of monomer | Have two or more types of monomers |
| Often have a simple structure | Have a complex structure |
| Examples include PVC, polyethylene, polypropylene, polystyrene, etc. | Examples include SEBS (styrene-ethylene-butylene-styrene), PEVA (polyethylene-vinyl acetate), etc. |

Some aspects of the technology disclosed herein relate to techniques for screening homopolymers, copolymers or blends for fabrication. A computing machine stores, in a data repository, a plurality of data points. Each data point comprises a structural repeating unit (SRU) and at least one material property value for the SRU. Each SRU is a homopolymer SRU, a copolymer component SRU or a blend component SRU. The computing machine determines a fingerprint for at least a subset of the SRUs in the data repository. The computing machine stores, in the data repository, each determined fingerprint in conjunction with a corresponding SRU. The computing machine generates, using at least a subset of the plurality of data points in the data repository, a quantitative modeling engine to predict material property values, based on SRUs, for homopolymers, copolymers or blends. The quantitative modeling engine is based, at least in part, on the fingerprints. The computing machine identifies, using the quantitative modeling engine, at least one homopolymer SRU, copolymer SRU set or blend SRU set that has a material property value within a given range. At least one homopolymer SRU, copolymer component SRU (e.g., member of the copolymer SRU set) or blend component SRU (e.g., member of the blend SRU set) is selected from a set of SRUs that is different from the SRUs represented by the plurality of data points in the data repository. The computing machine provides an output representing the identified at least one homopolymer SRU, copolymer SRU set, or blend SRU set.

As used herein, the term "convolutional neural network" or "CNN" may refer, among other things, to a neural network that is comprised of one or more convolutional layers (often with a subsampling operation) and then followed by one or more fully connected layers as in a standard multilayer neural network. In some cases, the architecture of a CNN is designed to take advantage of the 2D structure of an input image (or other 2D input such as a speech signal). This is achieved with local connections and tied weights followed by some form of pooling which results in translation invariant features. In some cases, CNNs are easier to train and have many fewer parameters than fully connected networks with the same number of hidden units. In some embodiments, a CNN includes multiple hidden layers and, therefore, may be referred to as a deep neural network (DNN). CNNs are generally described in "ImageNet Classification with Deep Convolutional Neural Networks," part of "Advances in Neural Information Processing Systems 25" (NIPS 2012) by Alex Krizhevsky, Ilya Sutskever, and Geoffrey E. Hinton, available at: papers.nips.cc/paper/4824-imagenet-classification-with-deep-convolutional-neural-network, last visited 28 Aug. 2019, the entire content of which is incorporated herein by reference.

As used herein, the phrase "computing machine" encompasses its plain and ordinary meaning. A computing machine may include, among other things, a single machine with a processor and a memory or multiple machines that have access to one or more processors or one or more memories, sequentially or in parallel. A server may be a computing machine. A client device may be a computing machine. A data repository may be a computing machine.

Throughout this document, some method(s) (e.g., in FIG. 7, FIG. 8, and FIG. 9) are described as being implemented serially and in a given order. However, unless explicitly stated otherwise, the operations of the method(s) may be performed in any order. In some cases, two or more operations of the method(s) may be performed in parallel using any known parallel processing techniques. In some cases, some of the operation(s) may be skipped and/or replaced with other operations. Furthermore, skilled persons in the relevant art may recognize other operation(s) that may be performed in conjunction with the operation(s) of the method(s) disclosed herein.

FIG. 1 illustrates the training and use of a machine-learning program, according to some example embodiments. In some example embodiments, machine-learning programs (MLPs), also referred to as machine-learning algorithms or tools, are utilized to perform operations associated with machine learning tasks, such as image recognition or machine translation.

Machine learning (ML) is a field of study that gives computers the ability to learn without being explicitly programmed. Machine learning explores the study and construction of algorithms, also referred to herein as tools, which may learn from existing data and make predictions about new data. Such machine-learning tools operate by building a model from example training data 112 in order to make data-driven predictions or decisions expressed as outputs or assessments 120. Although example embodiments are presented with respect to a few machine-learning tools, the principles presented herein may be applied to other machine-learning tools.

In some example embodiments, different machine-learning tools may be used. For example, Logistic Regression (LR), Naive-Bayes, Random Forest (RF), neural networks (NN), matrix factorization, and Support Vector Machines (SVM) tools may be used for classifying or scoring job postings.

Two common types of problems in machine learning are classification problems and regression problems. Classification problems, also referred to as categorization problems, aim at classifying items into one of several category values (for example, is this object an apple or an orange). Regression algorithms aim at quantifying some items (for example, by providing a value that is a real number). The machine-learning algorithms utilize the training data 112 to find correlations among identified features 102 that affect the outcome.

The machine-learning algorithms utilize features 102 for analyzing the data to generate assessments 120. A feature 102 is an individual measurable property of a phenomenon being observed. The concept of a feature is related to that of an explanatory variable used in statistical techniques such as linear regression. Choosing informative, discriminating, and independent features is important for effective operation of the MLP in pattern recognition, classification, and regression. Features may be of different types, such as numeric features, strings, and graphs.

In one example embodiment, the features 102 may be of different types and may include one or more of words of the message 103, message concepts 104, communication history 105, past user behavior 106, subject of the message 107, other message attributes 108, sender 109, and user data 110.

The machine-learning algorithms utilize the training data 112 to find correlations among the identified features 102 that affect the outcome or assessment 120. In some example embodiments, the training data 112 includes labeled data, which is known data for one or more identified features 102 and one or more outcomes, such as detecting communication patterns, detecting the meaning of the message, generating a summary of the message, detecting action items in the message, detecting urgency in the message, detecting a relationship of the user to the sender, calculating score attributes, calculating message scores, etc.

With the training data 112 and the identified features 102, the machine-learning tool is trained at operation 114. The machine-learning tool appraises the value of the features 102 as they correlate to the training data 112. The result of the training is the trained machine-learning program 116.

When the machine-learning program 116 is used to perform an assessment, new data 118 is provided as an input to the trained machine-learning program 116, and the machine-learning program 116 generates the assessment 120 as output. For example, when a message is checked for an action item, the machine-learning program utilizes the message content and message metadata to determine if there is a request for an action in the message.

Machine learning techniques train models to accurately make predictions on data fed into the models (e.g., what was said by a user in a given utterance; whether a noun is a person, place, or thing; what the weather will be like tomorrow). During a learning phase, the models are developed against a training dataset of inputs to optimize the models to correctly predict the output for a given input. Generally, the learning phase may be supervised, semi-supervised, or unsupervised; indicating a decreasing level to which the "correct" outputs are provided in correspondence to the training inputs. In a supervised learning phase, all of the outputs are provided to the model and the model is directed to develop a general rule or algorithm that maps the input to the output. In contrast, in an unsupervised learning phase, the desired output is not provided for the inputs so that the model may develop its own rules to discover relationships within the training dataset. In a semi-supervised learning phase, an incompletely labeled training set is provided, with some of the outputs known and some unknown for the training dataset.

Models may be run against a training dataset for several epochs (e.g., iterations), in which the training dataset is repeatedly fed into the model to refine its results. For example, in a supervised learning phase, a model is developed to predict the output for a given set of inputs and is evaluated over several epochs to more reliably provide the output that is specified as corresponding to the given input for the greatest number of inputs for the training dataset. In another example, for an unsupervised learning phase, a model is developed to cluster the dataset into n groups and is evaluated over several epochs as to how consistently it places a given input into a given group and how reliably it produces the n desired clusters across each epoch.

Once an epoch is run, the models are evaluated and the values of their variables are adjusted to attempt to better refine the model in an iterative fashion. In various aspects, the evaluations are biased against false negatives, biased against false positives, or evenly biased with respect to the overall accuracy of the model. The values may be adjusted in several ways depending on the machine learning technique used. For example, in a genetic or evolutionary algorithm, the values for the models that are most successful in predicting the desired outputs are used to develop values for models to use during the subsequent epoch, which may include random variation/mutation to provide additional data points. One of ordinary skill in the art will be familiar with several other machine learning algorithms that may be applied with the present disclosure, including linear regression, random forests, decision tree learning, neural networks, deep neural networks, etc.

Each model develops a rule or algorithm over several epochs by varying the values of one or more variables affecting the inputs to more closely map to a desired result, but as the training dataset may be varied, and is preferably very large, perfect accuracy and precision may not be achievable. A number of epochs that make up a learning phase, therefore, may be set as a given number of trials or a fixed time/computing budget, or may be terminated before that number/budget is reached when the accuracy of a given model is high enough or low enough or an accuracy plateau has been reached. For example, if the training phase is designed to run n epochs and produce a model with at least 95% accuracy, and such a model is produced before the nth epoch, the learning phase may end early and use the produced model satisfying the end-goal accuracy threshold. Similarly, if a given model is inaccurate enough to satisfy a random chance threshold (e.g., the model is only 55% accurate in determining true/false outputs for given inputs), the learning phase for that model may be terminated early, although other models in the learning phase may continue training. Similarly, when a given model continues to provide similar accuracy or vacillate in its results across multiple epochs—having reached a performance plateau—the learning phase for the given model may terminate before the epoch number/computing budget is reached.

Once the learning phase is complete, the models are finalized. In some example embodiments, models that are finalized are evaluated against testing criteria. In a first example, a testing dataset that includes known outputs for its inputs is fed into the finalized models to determine an accuracy of the model in handling data that it has not been trained on. In a second example, a false positive rate or false negative rate may be used to evaluate the models after finalization. In a third example, a delineation between data clusterings is used to select a model that produces the clearest bounds for its clusters of data.

FIG. 2 illustrates an example neural network 204, in accordance with some embodiments. As shown, the neural network 204 receives, as input, source domain data 202. The input is passed through a plurality of layers 206 to arrive at an output. Each layer 206 includes multiple neurons 208. The neurons 208 receive input from neurons of a previous layer and apply weights to the values received from those neurons in order to generate a neuron output. The neuron outputs from the final layer 206 are combined to generate the output of the neural network 204.

As illustrated at the bottom of FIG. 2, the input is a vector x. The input is passed through multiple layers 206, where weights $W_1, W_2, \ldots, W_i$ are applied to the input to each layer to arrive at $f^1(x), f^2(x), \ldots, f^{-1}(x)$, until finally the output f(x) is computed. The weights are established (or adjusted) through learning and training of the network. As shown, each of the weights $W_1, W_2, \ldots, W_i$ is a vector. However, in some embodiments, the each of the weights may be a scalar.

Neural networks utilize features for analyzing the data to generate assessments (e.g., recognize units of speech). A feature is an individual measurable property of a phenomenon being observed. The concept of feature is related to that of an explanatory variable used in statistical techniques such as linear regression. Further, deep features represent the output of nodes in hidden layers of the deep neural network.

A neural network, sometimes referred to as an artificial neural network, is a computing system/apparatus based on consideration of neural networks of biological brains. Such systems/apparatus progressively improve performance, which is referred to as learning, to perform tasks, typically without task-specific programming. For example, in image recognition, a neural network may be taught to identify images that contain an object by analyzing example images that have been tagged with a name for the object and, having learned the object and name, may use the analytic results to identify the object in untagged images. A neural network is based on a collection of connected units called neurons, where each connection, called a synapse, between neurons can transmit a unidirectional signal with an activating strength (e.g., a weight as shown in FIG. 2) that varies with the strength of the connection. The weight applied for the output of a first neuron at the input of a second neuron may correspond to the activating strength. The receiving neuron can activate and propagate a signal to downstream neurons connected to it, typically based on whether the combined incoming signals, which are from potentially many transmitting neurons, are of sufficient strength, where strength is a parameter.

A deep neural network (DNN) is a stacked neural network, which is composed of multiple layers. The layers are composed of nodes, which are locations where computation occurs, loosely patterned on a neuron in the biological brain, which fires when it encounters sufficient stimuli. A node combines input from the data with a set of coefficients, or weights, that either amplify or dampen that input, which assigns significance to inputs for the task the algorithm is trying to learn. These input-weight products are summed, and the sum is passed through what is called a node's activation function, to determine whether and to what extent that signal progresses further through the network to affect the ultimate outcome. A DNN uses a cascade of many layers of non-linear processing units for feature extraction and transformation. Each successive layer uses the output from the previous layer as input. Higher-level features are derived from lower-level features to form a hierarchical representation. The layers following the input layer may be convolution layers that produce feature maps that are filtering results of the inputs and are used by the next convolution layer.

In training of a DNN architecture, a regression, which is structured as a set of statistical processes for estimating the relationships among variables, can include a minimization of a cost function. The cost function may be implemented as a function to return a number representing how well the neural network performed in mapping training examples to correct output. In training, if the cost function value is not within a pre-determined range, based on the known training images, backpropagation is used, where backpropagation is a common method of training artificial neural networks that are used with an optimization method such as a stochastic gradient descent (SGD) method.

Use of backpropagation can include propagation and weight update. When an input is presented to the neural network, it is propagated forward through the neural network, layer by layer, until it reaches the output layer. The output of the neural network is then compared to the desired output, using the cost function, and an error value is calculated for each of the nodes in the output layer. The error values are propagated backwards, starting from the output, until each node has an associated error value which roughly represents its contribution to the original output. Backpropagation can use these error values to calculate the gradient of the cost function with respect to the weights in the neural network. The calculated gradient is fed to the selected optimization method to update the weights to attempt to minimize the cost function.

Figure 3:
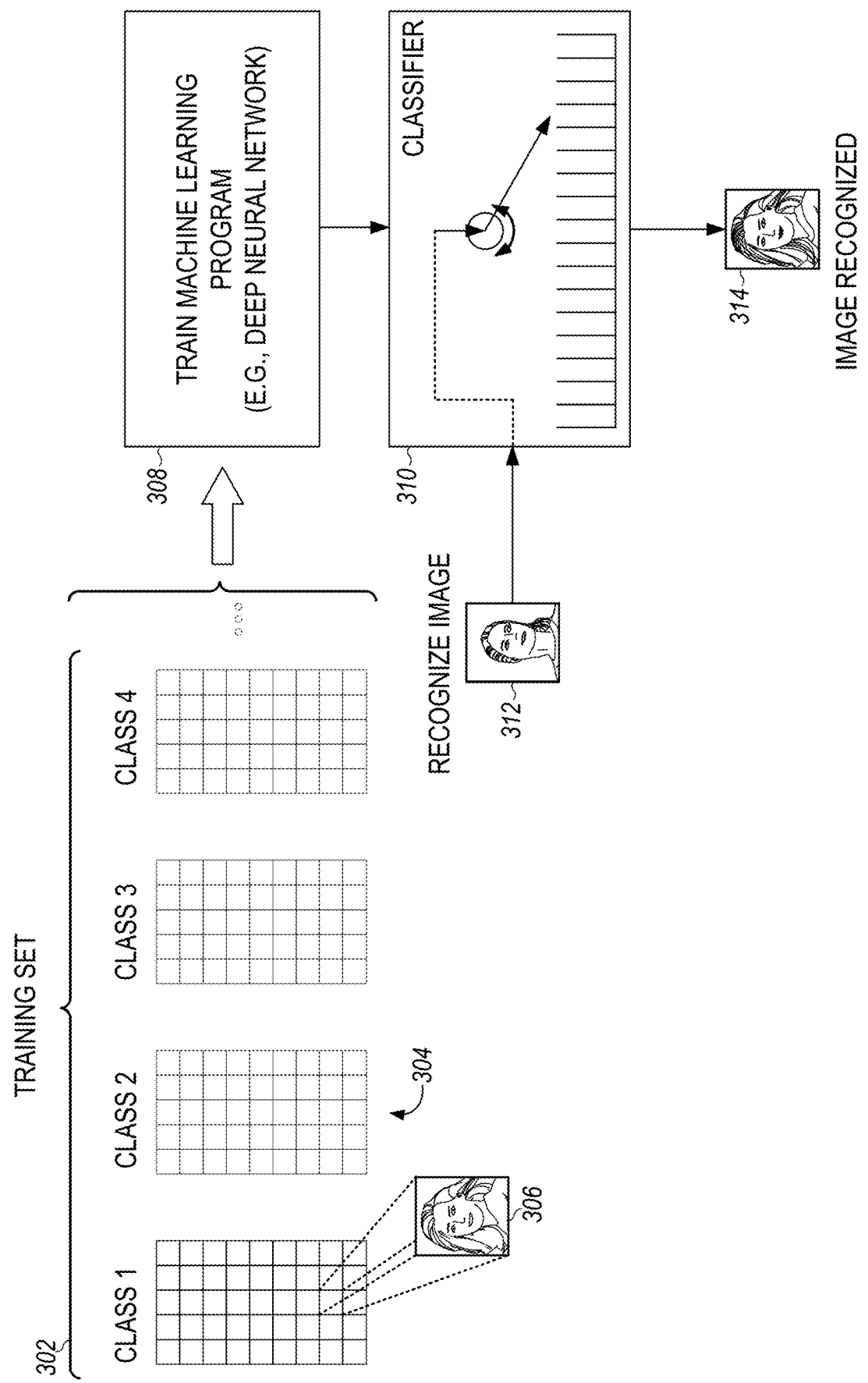
FIG. 3 illustrates the training of an image recognition machine learning program, in accordance with some embodiments.

FIG. 3 illustrates the training of an image recognition machine learning program, in accordance with some embodiments. The machine learning program may be implemented at one or more computing machines. Block 302 illustrates a training set, which includes multiple classes 304. Each class 304 includes multiple images 306 associated with the class. Each class 304 may correspond to a type of object in the image 306 (e.g., a digit 0-9, a man or a woman, a cat or a dog, etc.). In one example, the machine learning program is trained to recognize images of the presidents of the United States, and each class corresponds to each president (e.g., one class corresponds to Donald Trump, one class corresponds to Barack Obama, one class corresponds to George W. Bush, etc.). At block 308 the machine learning program is trained, for example, using a deep neural network. At block 310, the trained classifier, generated by the training of block 308, recognizes an image 312, and at block 314 the image is recognized. For example, if the image 312 is a photograph of Bill Clinton, the classifier recognizes the image as corresponding to Bill Clinton at block 314.

FIG. 3 illustrates the training of a classifier, according to some example embodiments. A machine learning algorithm is designed for recognizing faces, and a training set 302 includes data that maps a sample to a class 304 (e.g., a class includes all the images of purses). The classes may also be referred to as labels. Although embodiments presented herein are presented with reference to object recognition, the same principles may be applied to train machine-learning programs used for recognizing any type of items.

The training set 302 includes a plurality of images 306 for each class 304 (e.g., image 306), and each image is associated with one of the categories to be recognized (e.g., a class). The machine learning program is trained 308 with the training data to generate a classifier 310 operable to recognize images. In some example embodiments, the machine learning program is a DNN.

When an input image 312 is to be recognized, the classifier 310 analyzes the input image 312 to identify the class (e.g., class 314) corresponding to the input image 312.

Figure 4:
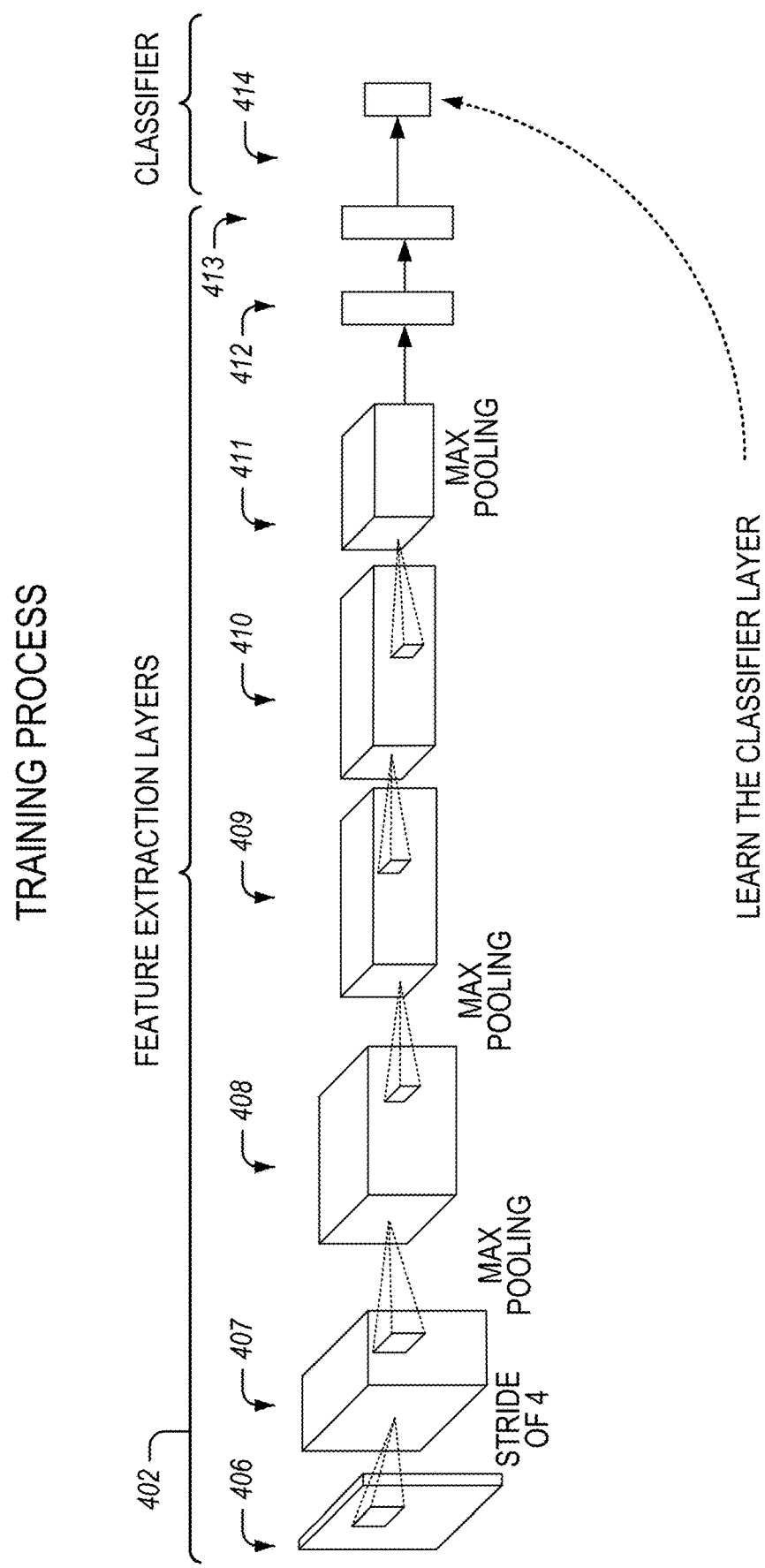
FIG. 4 illustrates the feature-extraction process and classifier training, in accordance with some embodiments.

FIG. 4 illustrates the feature-extraction process and classifier training, according to some example embodiments. Training the classifier may be divided into feature extraction layers 402 and classifier layer 414. Each image is analyzed in sequence by a plurality of layers 406-413 in the feature-extraction layers 402.

With the development of deep convolutional neural networks, the focus in face recognition has been to learn a good face feature space, in which faces of the same person are close to each other and faces of different persons are far away from each other. For example, the verification task with the LFW (Labeled Faces in the Wild) dataset has been often used for face verification.

Many face identification tasks (e.g., MegaFace and LFW) are based on a similarity comparison between the images in the gallery set and the query set, which is essentially a K-nearest-neighborhood (KNN) method to estimate the person's identity. In the ideal case, there is a good face feature extractor (inter-class distance is always larger than the intra-class distance), and the KNN method is adequate to estimate the person's identity.

Feature extraction is a process to reduce the amount of resources required to describe a large set of data. When performing analysis of complex data, one of the major problems stems from the number of variables involved. Analysis with a large number of variables generally requires a large amount of memory and computational power, and it may cause a classification algorithm to overfit to training samples and generalize poorly to new samples. Feature extraction is a general term describing methods of constructing combinations of variables to get around these large data-set problems while still describing the data with sufficient accuracy for the desired purpose.

In some example embodiments, feature extraction starts from an initial set of measured data and builds derived values (features) intended to be informative and non-redundant, facilitating the subsequent learning and generalization operations. Further, feature extraction is related to dimensionality reduction, such as reducing large vectors (sometimes with very sparse data) to smaller vectors capturing the same, or similar, amount of information.

Determining a subset of the initial features is called feature selection. The selected features are expected to contain the relevant information from the input data, so that the desired task can be performed by using this reduced representation instead of the complete initial data. DNN utilizes a stack of layers, where each layer performs a function. For example, the layer could be a convolution, a non-linear transform, the calculation of an average, etc. Eventually this DNN produces outputs by classifier 414. In FIG. 4, the data travels from left to right and the features are extracted. The goal of training the neural network is to find the weights for all the layers that make them adequate for the desired task.

As shown in FIG. 4, a "stride of 4" filter is applied at layer 406, and max pooling is applied at layers 407-413. The stride controls how the filter convolves around the input volume. "Stride of 4" refers to the filter convolving around the input volume four units at a time. Max pooling refers to down-sampling by selecting the maximum value in each max pooled region.

In some example embodiments, the structure of each layer is predefined. For example, a convolution layer may contain small convolution kernels and their respective convolution parameters, and a summation layer may calculate the sum, or the weighted sum, of two pixels of the input image. Training assists in defining the weight coefficients for the summation.

One way to improve the performance of DNNs is to identify newer structures for the feature-extraction layers, and another way is by improving the way the weights are identified at the different layers for accomplishing a desired task. The challenge is that for a typical neural network, there may be millions of weights to be optimized. Trying to optimize all these weights from scratch may take hours, days, or even weeks, depending on the amount of computing resources available and the amount of data in the training set.

Figure 5:
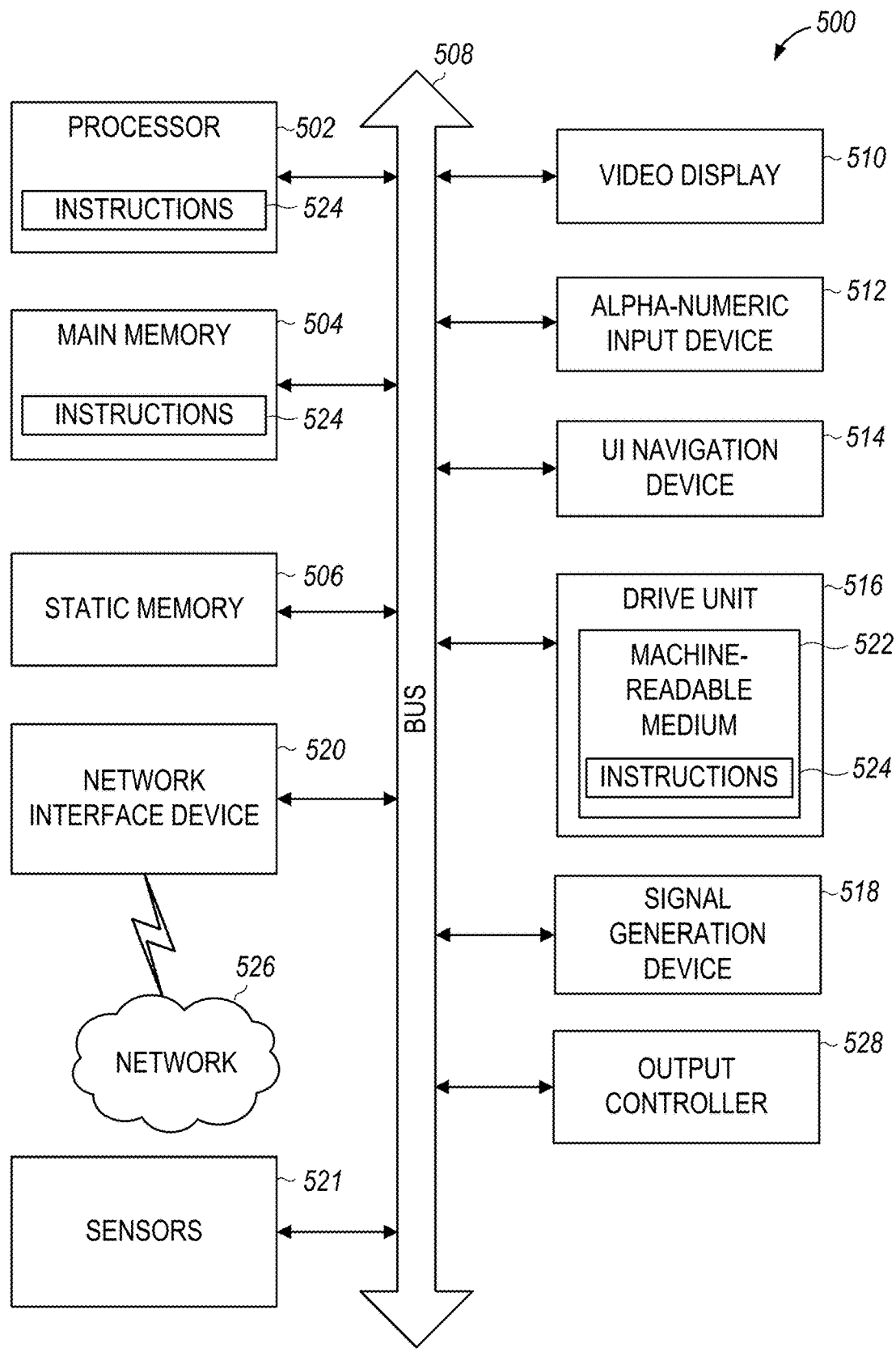
FIG. 5 is a block diagram of a computing machine, in accordance with some embodiments.

FIG. 5 illustrates a circuit block diagram of a computing machine 500 in accordance with some embodiments. In some embodiments, components of the computing machine 500 may store or be integrated into other components shown in the circuit block diagram of FIG. 5. For example, portions of the computing machine 500 may reside in the processor 502 and may be referred to as "processing circuitry." Processing circuitry may include processing hardware, for example, one or more central processing units (CPUs), one or more graphics processing units (GPUs), and the like. In alternative embodiments, the computing machine 500 may operate as a standalone device or may be connected (e.g., networked) to other computers. In a networked deployment, the computing machine 500 may operate in the capacity of a server, a client, or both in server-client network environments. In an example, the computing machine 500 may act as a peer machine in peer-to-peer (P2P) (or other distributed) network environment. In this document, the phrases P2P, device-to-device (D2D) and sidelink may be used interchangeably. The computing machine 500 may be a specialized computer, a personal computer (PC), a tablet PC, a personal digital assistant (PDA), a mobile telephone, a smart phone, a web appliance, a network router, switch or bridge, or any machine capable of executing instructions (sequential or otherwise) that specify actions to be taken by that machine.

Examples, as described herein, may include, or may operate on, logic or a number of components, modules, or mechanisms. Modules and components are tangible entities (e.g., hardware) capable of performing specified operations and may be configured or arranged in a certain manner. In an example, circuits may be arranged (e.g., internally or with respect to external entities such as other circuits) in a specified manner as a module. In an example, the whole or part of one or more computer systems/apparatus (e.g., a standalone, client or server computer system) or one or more hardware processors may be configured by firmware or software (e.g., instructions, an application portion, or an application) as a module that operates to perform specified operations. In an example, the software may reside on a machine readable medium. In an example, the software, when executed by the underlying hardware of the module, causes the hardware to perform the specified operations.

Accordingly, the term "module" (and "component") is understood to encompass a tangible entity, be that an entity that is physically constructed, specifically configured (e.g., hardwired), or temporarily (e.g., transitorily) configured (e.g., programmed) to operate in a specified manner or to perform part or all of any operation described herein. Considering examples in which modules are temporarily configured, each of the modules need not be instantiated at any one moment in time. For example, where the modules comprise a general-purpose hardware processor configured using software, the general-purpose hardware processor may be configured as respective different modules at different times. Software may accordingly configure a hardware processor, for example, to constitute a particular module at one instance of time and to constitute a different module at a different instance of time.

The computing machine 500 may include a hardware processor 502 (e.g., a central processing unit (CPU), a GPU, a hardware processor core, or any combination thereof), a main memory 504 and a static memory 506, some or all of which may communicate with each other via an interlink (e.g., bus) 508. Although not shown, the main memory 504 may contain any or all of removable storage and non-removable storage, volatile memory or non-volatile memory. The computing machine 500 may further include a video display unit 510 (or other display unit), an alphanumeric input device 512 (e.g., a keyboard), and a user interface (UI) navigation device 514 (e.g., a mouse). In an example, the display unit 510, input device 512 and UI navigation device 514 may be a touch screen display. The computing machine 500 may additionally include a storage device (e.g., drive unit) 516, a signal generation device 518 (e.g., a speaker), a network interface device 520, and one or more sensors 521, such as a global positioning system (GPS) sensor, compass, accelerometer, or other sensor. The computing machine 500 may include an output controller 528, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The drive unit 516 (e.g., a storage device) may include a machine readable medium 522 on which is stored one or more sets of data structures or instructions 524 (e.g., software) embodying or utilized by any one or more of the techniques or functions described herein. The instructions 524 may also reside, completely or at least partially, within the main memory 504, within static memory 506, or within the hardware processor 502 during execution thereof by the computing machine 500. In an example, one or any combination of the hardware processor 502, the main memory 504, the static memory 506, or the storage device 516 may constitute machine readable media.

While the machine readable medium 522 is illustrated as a single medium, the term "machine readable medium" may include a single medium or multiple media (e.g., a centralized or distributed database, and/or associated caches and servers) configured to store the one or more instructions 524.

The term "machine readable medium" may include any medium that is capable of storing, encoding, or carrying instructions for execution by the computing machine 500 and that cause the computing machine 500 to perform any one or more of the techniques of the present disclosure, or that is capable of storing, encoding or carrying data structures used by or associated with such instructions. Non-limiting machine-readable medium examples may include solid-state memories, and optical and magnetic media. Specific examples of machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; Random Access Memory (RAM); and CD-ROM and DVD-ROM disks. In some examples, machine readable media may include non-transitory machine-readable media. In some examples, machine readable media may include machine readable media that is not a transitory propagating signal.

The instructions 524 may further be transmitted or received over a communications network 526 using a transmission medium via the network interface device 520 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, a Long Term Evolution (LTE) family of standards, a Universal Mobile Telecommunications System (UMTS) family of standards, peer-to-peer (P2P) networks, among others. In an example, the network interface device 520 may include one or more physical jacks (e.g., Ethernet, coaxial, or phone jacks) or one or more antennas to connect to the communications network 526.

Figure 6:
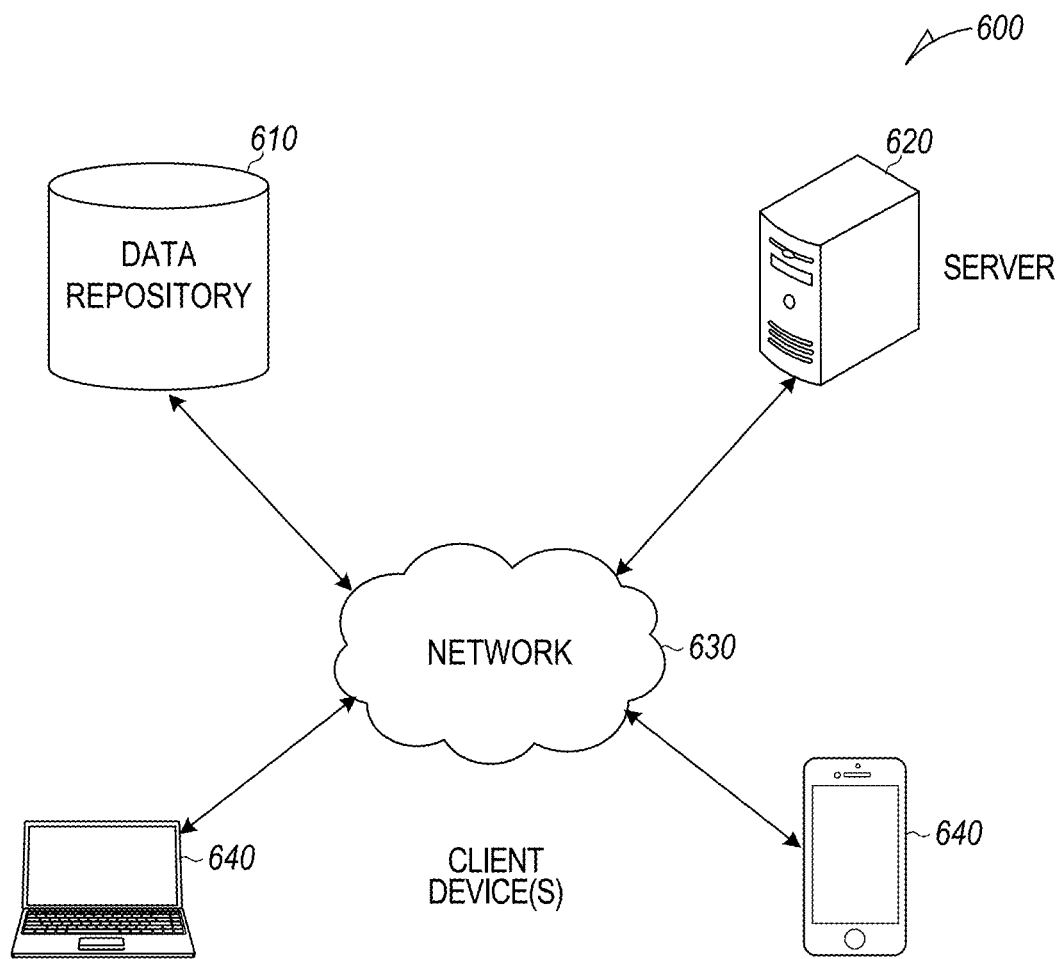
FIG. 6 illustrates an example network-based system for screening homopolymers, copolymers or blends for fabrication, in accordance with some embodiments.

FIG. 6 illustrates an example network-based system 600 for screening homopolymers, copolymers or blends for fabrication, in accordance with some embodiments.

As shown, the system 600 includes a data repository 610, a server 620, and client device(s) 630 configured to communicate with one another via a network 640. The network 640 may include one or more of the internet, an intranet, a local area network, a wide area network, a Wi-Fi network, a cellular network, a virtual private network, and the like.

The client device(s) 630 may include end-user device(s) that include processing circuitry and memory. For example, a client device 630 may be a laptop computer, a desktop computer, a mobile phone, a tablet computer, a smart watch, and the like. Each client device 630 is configured to present output to a user, for example, via a display device, an audio speaker, and the like. Each client device 630 is configured to receive user input, for example, via a touch screen, a keyboard, a mouse, a camera, a microphone, and the like.

The data repository 610 may be a database or any other data storage unit. In some embodiments, the data repository stores a plurality of data points. Each data point comprises a structural repeating unit (SRU) and at least one material property value for the SRU. Each SRU is a homopolymer SRU, a copolymer component SRU or a blend component SRU.

The server 620 may include a single server, multiple servers or a server farm. The server may perform one or more of the techniques disclosed in conjunction with FIG. 7, FIG. 8 or FIG. 9.

In some embodiments, the server 620 determines a fingerprint for at least a subset of the SRUs in the data repository 610. The server 620, stores, in the data repository 610, each determined fingerprint in conjunction with a corresponding SRU. The server 620 generates, using at least a subset of the plurality of data points in the data repository 610, a quantitative modeling engine to predict material property values, based on SRUs, for homopolymers, copolymers or blends. The quantitative modeling engine is based, at least in part, on the fingerprints. The quantitative modeling engine may reside at the server and may be implemented using only software, only hardware, or a combination of software and hardware. The server 620 identifies, using the quantitative modeling engine, at least one homopolymer SRU, copolymer SRU set or blend SRU set that has a material property value within a given range. At least one homopolymer SRU, copolymer component SRU or blend component SRU is selected from a set of SRUs that is different from the SRUs represented by the plurality of data points in the data repository. The server provides (e.g., via the network 630 to a client device 640 for display thereat) an output representing the identified at least one homopolymer SRU, copolymer SRU set or blend SRU set.

FIG. 6 illustrates an example system 600 with a single data repository 610, a single server 620, and two client devices 640. However, some aspects of the technology described herein may include multiple servers, data repositories or client devices. In some aspects, a single computing machine performs the functions of two or more of the data repository 610, the server 620, and the client device 640. In some aspects, a single computing machine performs the functions of all three of the data repository 610, the server 620, and the client device 630. As shown in FIG. 6, the data repository 610, the server 620, and the client device 640 communicate via the network 630. However, in some cases, two or more of these computing machines can be coupled by a direct wired or direct wireless connection in addition to or in place of the network 640. As illustrated in FIG. 6, the machines 610, 620, and 640 communicate over a single network 630. However, in alternative embodiments, multiple different networks (or direct wired or wireless connections) may be used in place of the single network 630.

Figure 7:
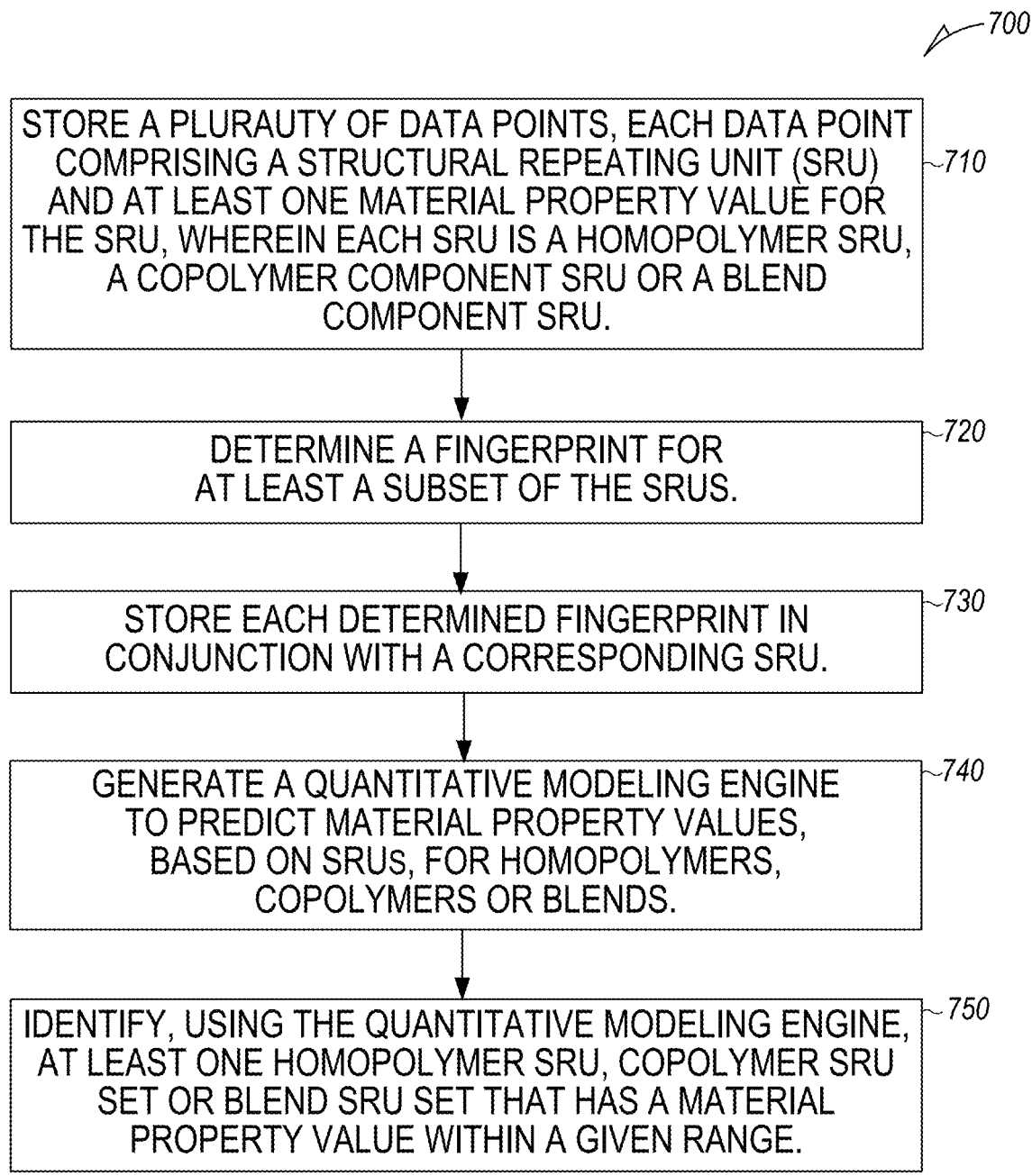
FIG. 7 is a flow chart illustrating an example method for screening homopolymers, copolymers or blends for fabrication, in accordance with some embodiments.

FIG. 7 is a flow chart illustrating an example method 700 for screening homopolymers, copolymers or blends for fabrication, in accordance with some embodiments. The method 700 may be implemented by a computing machine, for example, the server 620 of FIG. 6 or the computing machine 500 of FIG. 5.

At operation 710, the computing machine stores, in a data repository (e.g., data repository 610 or an internal or external memory of the computing machine), a plurality of data points. Each data point includes a SRU and at least one material property value for the SRU. Each SRU is a homopolymer SRU, a copolymer component SRU or a blend component SRU. The material property corresponding to the material property value may be, for example, a refractive index, a density, a cohesive energy density, a solubility parameter or a surface tension.

At operation 720, the computing machine determines a fingerprint for at least a subset of the SRUs in the data repository. The fingerprint may be a chemical, structural or other fingerprint.

At operation 730, the computing machine stores, in the data repository, each determined fingerprint in conjunction with a corresponding SRU.

At operation 740, the computing machine generates, using at least a subset of the plurality of data points in the data repository, a quantitative modeling engine to predict material property values, based on SRUs, for homopolymers, copolymers or blends. The quantitative modeling engine is based, at least in part, on the fingerprints. The quantitative modeling engine may be stored at the computing machine and may be implemented using software, hardware or a combination of software and hardware. In some aspects, the quantitative modeling engine leverages one or more of: an artificial intelligence (AI) model, a genetic algorithm, a regression model, a decision tree, a random forest, a neural network, and a combinatorial model. The quantitative modeling engine may leverage the technologies described herein in conjunction with FIGS. 1-4.

At operation 750, the computing machine identifies, using the quantitative modeling engine, at least one homopolymer SRU, copolymer SRU set or blend SRU set that has a material property value within a given range. At least one homopolymer SRU, copolymer component SRU or blend component SRU is selected from a set of SRUs that is different from the SRUs represented by the plurality of data points in the data repository. In some cases, the computing machine provides an output representing the identified at least one homopolymer SRU, copolymer SRU set or blend SRU set. The output may be provided for storage in the data repository or another data store, for display via a display port of the computing machine, or for display at a remote machine (e.g., one or more of the client device(s) 640). The output may be transmitted, for display or storage, via a network (e.g., the network 630).

In some cases, the computing machine stores, in the data repository, the identified at least one homopolymer SRU, copolymer SRU set or blend SRU set in conjunction with a computed material property value for it.

In some embodiments, the quantitative modeling engine leverages a genetic algorithm. To identify at least one homopolymer SRU, copolymer SRU set or blend SRU set that has the material property value within the given range, the computing machine (e.g., executing the quantitative modeling engine) defines, for a test SRU population, attachment sites and side chains. Until the attachment sites are filled, the computing machine repeats: (i) attaching pseudo-randomly selected side chains to pseudo-randomly selected open attachment sites; (ii) identifying, using an objective function for the given material property, a subset of the population having the material property value within the given range; and (iii) adding the subset of the population to a result set. Upon determining that the attachment sites are filled, the computing machine provides an output representing at least a portion of the result set. The output may be provided for local or remote display or storage.

As used herein, the term "pseudo-random" encompasses its plain and ordinary meaning. A pseudo-random number may be a random number generated using a long (e.g., having more than one thousand or one million values) list of numbers (e.g., seeded by a clock function). The pseudo-random function solves the problem that a truly random algorithm cannot be implemented on a preprogrammed computing machine. The long list of numbers may include random numbers between 0 and 1. To select among n options (where n is a positive integer), the n options may be numbered from 0 to n−1. A pseudo-random number between 0 and 1 may be selected and multiplied by n, yielding a value m. The option numbered m is then selected.

In some aspects, the computing machine receives a copolymer or blend optimization request, which includes one or more representations of one or more SRUs of the copolymer or blend, at least one material property for optimization, and a target value for each material property for optimization. The copolymer or blend optimization request may be received, at the computing machine and from a client device, via a graphical user interface (GUI) accessible via an intranet. The GUI may be provided for display at the client device. Example GUIs are shown in FIGS. 10-14. The computing machine computes, using at least the quantitative modeling engine, an optimization result comprising at least one copolymer or blend structure. A computed value for each material property for optimization of at least one copolymer or blend structure is within a threshold percentage of the target value. The computing machine provides an output of the optimization result. The output may be provided for local or remote display or storage. In some cases, the output representing the optimization result includes a visual representation of the at least one copolymer or blend structure and the computed value for each material property for optimization.

The one or more representations of the one or more SRUs of the copolymer or blend comprise one or more SMILES (simplified molecular-input line-entry system) strings (or other descriptor strings), a CAS (Chemical Abstracts Service) number or a link (e.g., to a webpage) to purchase the copolymer or blend. The CAS number is a number that uniquely identifies each chemical substance. In some aspects, the computing machine is configured to look up a CAS number for any homopolymer in the output.

In some embodiments, if a synthesizing record for a homopolymer, copolymer or blend associated with the at least one homopolymer SRU, copolymer SRU set or blend SRU set is not available, the computing machine predicts, for the homopolymer, copolymer or blend, an ease of synthesizability. In some embodiments, the computing machine causes fabrication of a homopolymer, copolymer or blend that includes the identified at least one homopolymer SRU, copolymer SRU set or blend SRU set. In some examples, upon fabrication of the homopolymer, copolymer or blend, the computing machine receives, from a user, an experimentally verified material property value. The experimentally verified material property value is stored in the data repository.

The quantitative modeling engine is adjusted based on the experimentally verified material property value. For example, if the experimentally verified material property value is within the given range, the computing machine increases a confidence value associated with a computation of the quantitative modeling engine. If the experimentally verified material property value is not within the given range, the computing machine modifies the quantitative modeling engine based on the experimentally verified material property value.

The term "descriptor string" generally refers to a computer-interpretable string that can be used to represent each monomer, or combination of monomers. For example, if the at least one monomer includes methyl methacrylate, the monomer could be represented by any suitable descriptor string, including a simplified molecular-input line-entry system (SMILES) string (e.g., canonical SMILES, which for a monomer like methyl methacrylate would be CC(=C)C(=O)OC); an International Union of Pure and Applied Chemistry (IUPAC) name, which in the instance of methyl methacrylate would be methyl 2-methylprop-2-enoate; an international chemical identifier (InChI) or InChI key, which for methyl methacrylate would be 1S/C5H8O2/c1-4(2)5(6)7-3/h1H2,2-3H3 and VVQNEPGJFQJSBK-UHFFFAOYSA-N, respectively; molecular formula, which for methyl methacrylate would be $CH_2C(CH_3)COOCH_3$ or $C_5H_8O_2$; chemical abstracts (CAS) number, which for methyl methacrylate would be 9065-11-6 (from ChemIDplus) or 9011-14-7 (from European Chemicals Agency); a Unique Ingredient Identifier (UNII), which for methyl methacrylate would be 196OC77688; and the like. Methyl methacrylate is disclosed here as one example of a monomer. As skilled persons in the art would realize, other monomers may also be used with the technology described herein. Some other examples of molecules, structures, and smiles formulas are shown in Table 2. To represent SRUs with SMILES strings, some aspects specify the beginning and end points using * characters for the continuation of the chain (e.g., for methyl methacrylate it would be *C(C)(C(=O)OC)C*).

TABLE 2

Example Molecular Structures and SMILES formulas.

| Molecule | Structure | SMILES Formula |
|---|---|---|
| Dinitrogen | N≡N | N#N |
| Methyl isocyanate (MIC) | $CH_3$—N=C=O | CN=C=O |
| Copper(II) sulfate | $Cu^{2+}$ $SO_4^{2-}$ | [Cu+2]·[O—]S(=O)(=O)[O—] |

The SMILES is a specification in form of a line notation for describing the structure of chemical species using short ASCII strings. SMILES strings can be imported by most molecule editors for conversion back into two-dimensional drawings or three-dimensional models of the molecules. In terms of a graph-based computational procedure, SMILES is a string obtained by printing the symbol nodes encountered in a depth-first tree traversal of a chemical graph. The chemical graph is first trimmed to remove hydrogen atoms and cycles are broken to turn it into a spanning tree. Where cycles have been broken, numeric suffix labels are included to indicate the connected nodes. Parentheses are used to indicate points of branching on the tree. The resultant SMILES form depends on the choices: (i) of the bonds chosen to break cycles, (ii), and (iii) of the order in which branches are listed when encountered. A SMILES string is one example of a descriptor string that can be used to represent a chemical compound, such as a monomer in silico. A computer would then be able to interpret the monomer in such a way that it is clear which nodes would be joined to polymerize the monomer in silico. There would also be a way to determine the number of monomers that are going to be incorporated into a given polymer, thus determining the polymer's molecular weight-weight average ($M_w$) or number average ($M_n$); polydispersity, if applicable; and tacticity (e.g., syndiotactic and atactic), to the extent that any of these parameters could influence, among other things, load to failure and the crack growth velocity of the polymer based on the polymer structure.

Figure 8:
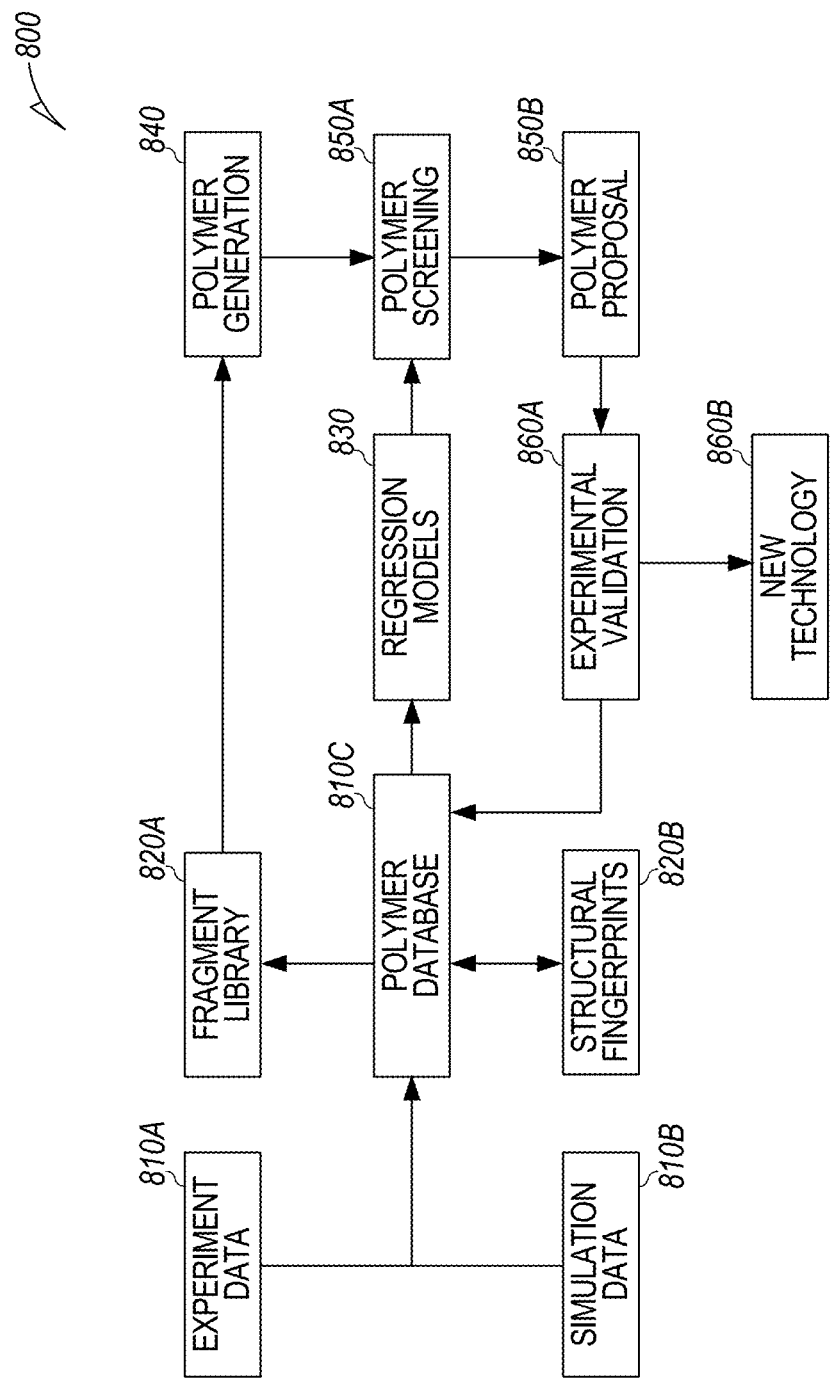
FIG. 8 is an example workflow for screening homopolymers, copolymers or blends for fabrication, in accordance with some embodiments.

FIG. 8 is an example workflow 800 for screening homopolymers, copolymers or blends for fabrication, in accordance with some embodiments. As shown, experiment data 810A and simulation data 810B are combined into a polymer database 810C (or, alternatively, other polymer data repository). The polymer database 810C is coupled with a fragment library 820A and structural fingerprints 820B. The polymer database 810C is used to generate regression models 830. The fragment library 820A is used for polymer generation 840. The regression model 830 and the polymer generation 840 provide output for polymer screening 850A. The polymer screening 850A results in a polymer proposal 850B. The polymer proposal 850B is subject to experimental validation 860A. The results of the experimental validation 860A are stored in the polymer database 810C and are used as a new technology 860B. It should be noted that the polymer database 810C is not limited to database technology. Any data repository (e.g., data repository 610) or data storage unit may be used.

The workflow 800 in FIG. 8 describes the general flow of information. (1) Existing data from experiments and simulations are compiled into a data repository. This data can be from either internal or external (literature) sources. Each data entry should include at least the polymer structural repeating unit (SRU) and at least one material property. (2)

Chemical structure data from the data repository are used to generate fingerprints, which are added back into the data repository. A library of chemical fragments is created from structures in the data repository. (3) Chemical fingerprints and properties from the data repository are used to train and validate various models (e.g., quantitative structure property relations, machine learning, deep learning) for predicting properties based on the input SRU. (4) In parallel to operation 3, chemical fragments from the chemical library are combined to generate a set of SRUs to be screened. (5) Generated SRUs are input into the models and the most promising candidates based on the given criteria are proposed to the experimental team. (6) Experiments (synthesis/acquisition, fabrication, characterization) are performed using the proposed polymers. Results are added back to the data repository and may lead to new technologies if the materials are promising. The workflow is modular in the sense that many different methods can be swapped based on the appropriate material and material property.

For data collection and storage, data is entered in a few different ways: internal data can be added to the database given appropriate labels; data that can be exported from open databases can be added directly to the data repository; and data from literature is manually extracted due to the unreliability of current automatic methods to accurately populate the appropriate fields.

In some aspects, these data are integrated into a data repository (e.g., relational database) using the SRUs as keys to link the different tables together. The SRUs are represented by both names and simplified molecular-input line-entry system (SMILES) strings, which is a common practice for organic material datasets. Once the SMILES strings are entered, they are used in the next step to generate fingerprints and descriptors, which are then added back into the database. Using the SMILES convention to build descriptors and models makes it simple to use. Material properties are typically continuous numerical variables, reported in specific units for each property.

The data repository may store not only experimental data, but also simulation data and the regression models. The simulation data is typically results from previously completed physics-based simulations, ranging from the electronic structure level up to the continuum scale; each of the scales individually can be used as powerful characterization tools. Once regression models are trained, the library of models is included within the database in its own table, including an identification tag, the property for which the model is used, as well as accuracy metrics (e.g., $R^2$ and mean squared error). The final trained models are saved to files that are called when the corresponding calculation is requested. These models are additionally referenced in the table of properties, where predicted properties from each of the models would be housed. Occasionally, with new data, the models may be refined and these updates to the model and the predicted values may be reflected within the data repository.

Fingerprints can be generated by parsing the SMILES string of the input SRU into a molecule object. Because molecules may be represented as graphs, with atoms as nodes and bonds as edges, techniques used to characterize graphs are well suited for this application. Information about each atom (e.g., atomic number, atomic mass, valence) and its neighbors can be quantified and/or hashed into certain descriptors that can describe the molecule as a whole. One example of such a fingerprint is the Morgan fingerprint, which is widely used for analytics of small molecules for drug design. Additional descriptors can be calculated given the connectivity of the atoms in the graph, such as the presence and number of certain functional groups within the SRU. Such descriptors are easily interpretable by chemists, which allows for the discovery of actionable trends. Fingerprints and descriptors can be mixed and matched as features used as input into the various regression models.

Given the set of SRUs, common backbone and side chain chemical structures are compiled into a library for future use in polymer generation. In some cases, this may be done manually. However, given the ability to distinguish side chains from backbones, automatic library population (e.g., using the artificial intelligence techniques described in conjunction with FIGS. 1-4) is possible.

Some embodiments leverage regression models.

One purpose of the regression models is to use the features calculated in the previous step to predict properties. The advantage these models have is their relatively low computational cost compared to physics-based computational techniques. In some embodiments, these properties (among others) may be used for calculation: refractive index, molar volume, density, cohesive energy density, solubility parameter, surface tension glass transition temperature, mechanical properties (e.g., Young's modulus, shear modulus), dielectric properties, and the like.

A wide range of regression models can be used in this workflow because of the diverse set of fingerprints and descriptors available. For example, simple linear regression models can be implemented based on a set of chemical descriptors; for each property, a different set of the most important descriptors can be selected. Another example would be using either a similar set of descriptors and/or a Morgan fingerprint as the input for a machine learning model, such as random forest or Gaussian process regression. Deep learning models such as graph convolutional neural networks can learn the features of the molecular structure on their own and additional features can be encoded to supplement them. Depending on the property, there will be different models that work best based on the amount and diversity of data. Before deciding which model to use, some aspects compare their accuracies for particular chemistries and select optimized models for chosen properties.

In addition, it is possible to use these models to predict properties of copolymers. Given a set of SRUs and their respective fractions, the calculator performs the appropriate interpolations for the properties of interest. The power of this comes not only to solve the forward engineering problem but also to solve the inverse problem. Given a set of SRUs and a set of desired properties, the fractions of each SRU in the copolymer can be calculated. For two SRUs, this is a simple single objective optimization because the two fractions adds up to one. For more than two SRUs, this becomes a constrained multiobjective optimization problem, where the fractions still add up to one but there are at least two independent parameters to fit. Metaheuristic methods such as particle swarm optimization can handle multiple objectives and yield a set of potential solutions that can be recommended for further testing.

When going from chemical mixtures (i.e., copolymers) to physical mixtures (i.e., blends), the interpolation becomes more complicated and requires specific models to be built. For blends of different polymer families, a model to fit the property value as a function of the blend ratio is necessary for each property or each set of properties where the behavior is expected to have similar physical origin. This method can also be used to further accuracy of the current interpolation routine for copolymers.

Figure 9:
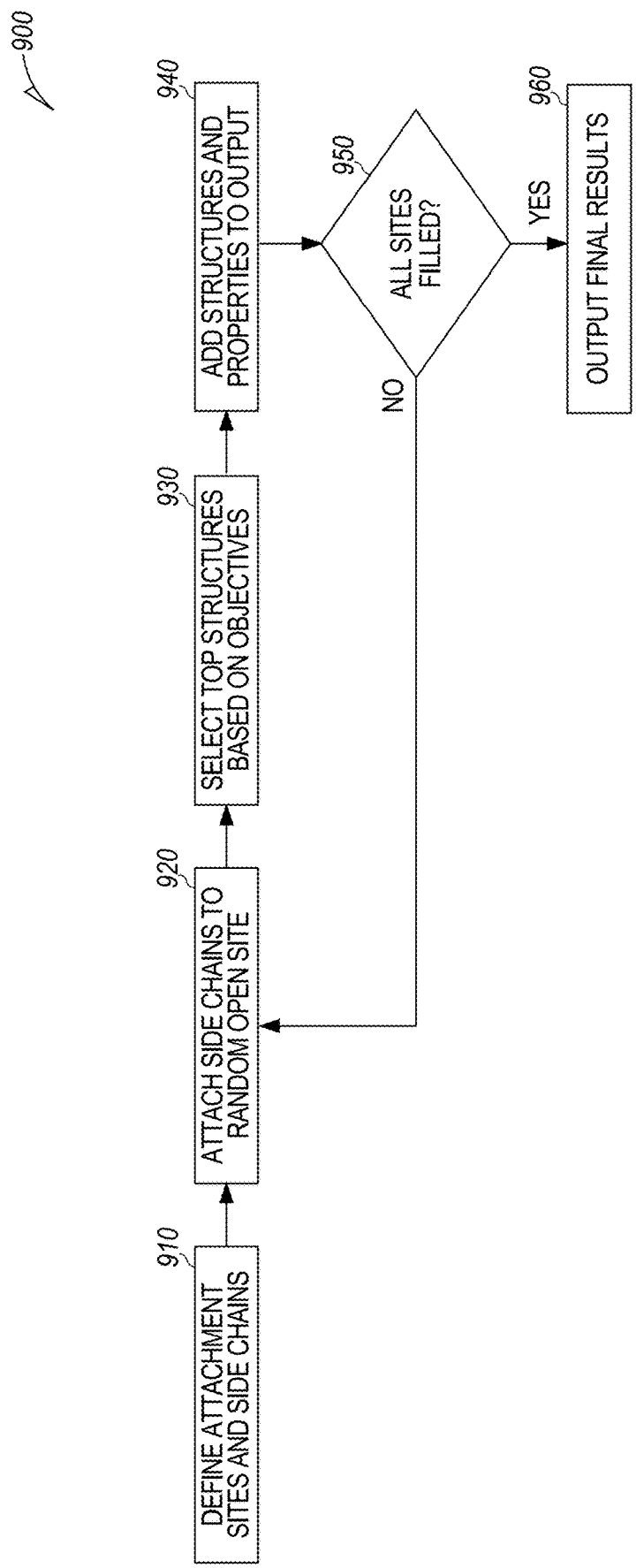
FIG. 9 is an example workflow for a genetic algorithm used in screening homopolymers, copolymers or blends for fabrication, in accordance with some embodiments.

FIG. 9 is an example workflow 900 for a genetic algorithm used in screening homopolymers, copolymers or blends for fabrication, in accordance with some embodiments. The workflow 900 may be completed by a computing machine (e.g., computing machine 500 or server 620).

At operation 910, the computing machine defines attachment sites and side chains.

At operation 920, the computing machine attaches side chains to random (or pseudo-random) open site(s).

At operation 930, the computing machine selects top (e.g., having an objective function value above a threshold) structures based on objectives.

At operation 940, the computing machine adds structures and properties to the output results.

At operation 950, the computing machine determines whether all sites are filled. If so, the workflow 900 continues to operation 960. If not, the workflow 900 returns to operation 920.

At operation 960, the computing machine outputs the final results. After operation 960, the workflow 900 ends.

Some aspects leverage combinatorial generation and screening.

Testing chemistries one at a time using the fast regression models is already useful. However, being able to test a large set of chemistries simultaneously is efficient for exploring the chemical space. The current implementation takes one backbone structure with an arbitrary number of attachment sites and an arbitrary number of side chain structures and combinatorially generates all possible structures. For example, if there are 4 sites and 10 different side chains, then $10^4$ or 10,000 structures would be generated. This emulates typical experimental design of polymers, where a particular backbone of interest is chosen as a starting point and small modifications are made to the structure to tweak certain properties.

For each structure generated, the properties of interest are calculated and a dataframe is populated with the SRU SMILES and the properties. This dataframe is then sub-sampled based on the defined property constraints to give a final set of potential polymers.

Another method for generating polymers is a genetic algorithm inspired by the family of evolutionary algorithms. In this method, instead of attaching to all defined sites at once, we step through and add to them one at a time. The general procedure is described in FIG. 9. The way that structures are chosen for the next iteration is based on the defined constraints of the screening. If there are ranges of properties specified, a certain defined percentage of structures generated in each round that satisfy all of the constraints are moved on to the next round. If properties are specified for minimization or maximization, the structures are sorted appropriately by the value of the property (if single property) or sorted by a weighted method (if multiple properties). A certain defined percentage of the top structures on the list are passed forward, as well as a certain defined percentage of the rest of the structures to maintain diversity.

Some aspects scale well for a larger numbers of sites, i.e. the number of calculations for the combinatorial screening scales as $$n_c^{n_s},$$

while that for the genetic algorithm scales as $$\sum_{i=1}^{n_s} f^{i-1} n_c^i$$

for the min or max case and is even better in the ranges case where it would be multiplied by some additional in each step based on how many of the structures satisfy the ranges. Here, $n_s$ is the number of attachment sites, $n_c$ is the number of side chains, and f is the fraction of structures to move on to the next round. For example, for 4 sites and 10 different side chains with the objective of maximizing density, the combinatorial screening would generate and calculate $10^4$ or 10000 polymers. However, the genetic algorithm that only keeps half of each generation would generate and calculate 10+50+250+1250=1560 polymers.

This genetic algorithm ultimately reduces computational time for cases where more than one site is targeted for substitution by more efficiently exploring the chemistries.

Polymers are an important component of many products. The choice of which polymers to incorporate in these cases depends on a large set of property constraints (e.g., on optical, mechanical, thermal properties). To find the ideal material for each application would typically take months of synthesis or acquisition, fabrication, and characterization; the materials that are tested are based solely on the scientists' experience and intuition, and only a few can be tested in parallel.

Computational techniques may be employed to overcome some of the challenges from the purely experimental approach. For example, atomistic simulation techniques can probe electronic structure (e.g., using density functional theory) or chain dynamics (e.g., using molecular dynamics) of polymers to calculate a set of properties for a polymer system. These approaches may have the high computational cost of including fine physical detail. Therefore, the number of simulations that can be run is also limited.

Some embodiments present a framework to apply data-driven methods and high throughput virtual screening as a way to narrow the large chemical space of polymers and accelerate discovery of promising candidates. This screening can be performed on a diverse set of properties, as opposed to existing methods in the literature that typically screen for a single property within a polymer family; the resulting polymer structures can be passed forward to either experiments or simulations. Some embodiments are directed to a computationally efficient method for calculating a set of polymer properties as a function of the chemical structure of a polymer structural repeating unit (SRU). This end-to-end workflow takes in the simple input of a string representation of the SRU and follows through to the prediction of properties. In addition, the framework includes a data repository that stores (1) data of chemical structures and associated properties obtained from experiments and simulations and (2) models built upon the data.

For most commercial applications, the polymer solution is a blend of homopolymers, which imparts it properties that individual homopolymers cannot exhibit. To aid with these applications, some aspects can (1) optimize blend ratios to achieve target properties, and (2) design blends to provide more optimal solutions.

Some aspects are directed to a GUI portal which enables calculations, optimization, and screening to be done directly by chemists with no computational background.

Some embodiments are directed to a modular workflow to perform prediction and high throughput screening of polymer properties. Some embodiments may include one or more of the following: generation of representative structural fingerprints for polymer structural repeating units (SRUs); selection of appropriate combinations of fingerprints for use in various data-driven regression models that use SRUs as inputs to predict properties; generation of a space of hypothetical polymer SRUs based on a library of backbone and side chain chemistries; addition of optimization methods, such as Monte Carlo and genetic algorithm, for faster screening; screening of the chemical space by calculation of properties of interest and filtration based on a set of defined criteria, including optical, mechanical, dielectric, and surface properties, and then potentially further screening for synthesizability and commercial availability; optimization of blend ratios to obtain desired properties; designing blends of polymers to obtain desired properties; a portal to perform these actions online in a tractable fashion; and a data repository containing polymer structures and properties as well as a library of models for predicting properties from structures.

Some aspects may include one or more of the following: a set of descriptors and fingerprints based on the chemical structure that can be appropriately selected for particular regression models, which allows for more flexibility when retraining models given data in new spaces; high throughput screening of polymer chemistries, which is orders of magnitude faster than typical experimental and physics-based simulation techniques toward finding materials of interest for new applications; screening technique that can also provide insight for copolymers and mixtures of polymers, which has previously not been explored; a portal that both modelers and experimentalists can use to interact with these capabilities.

FIGS. 10A-10B illustrate an example user interface for a calculation capability, in accordance with some embodiments.

Figure 11A:
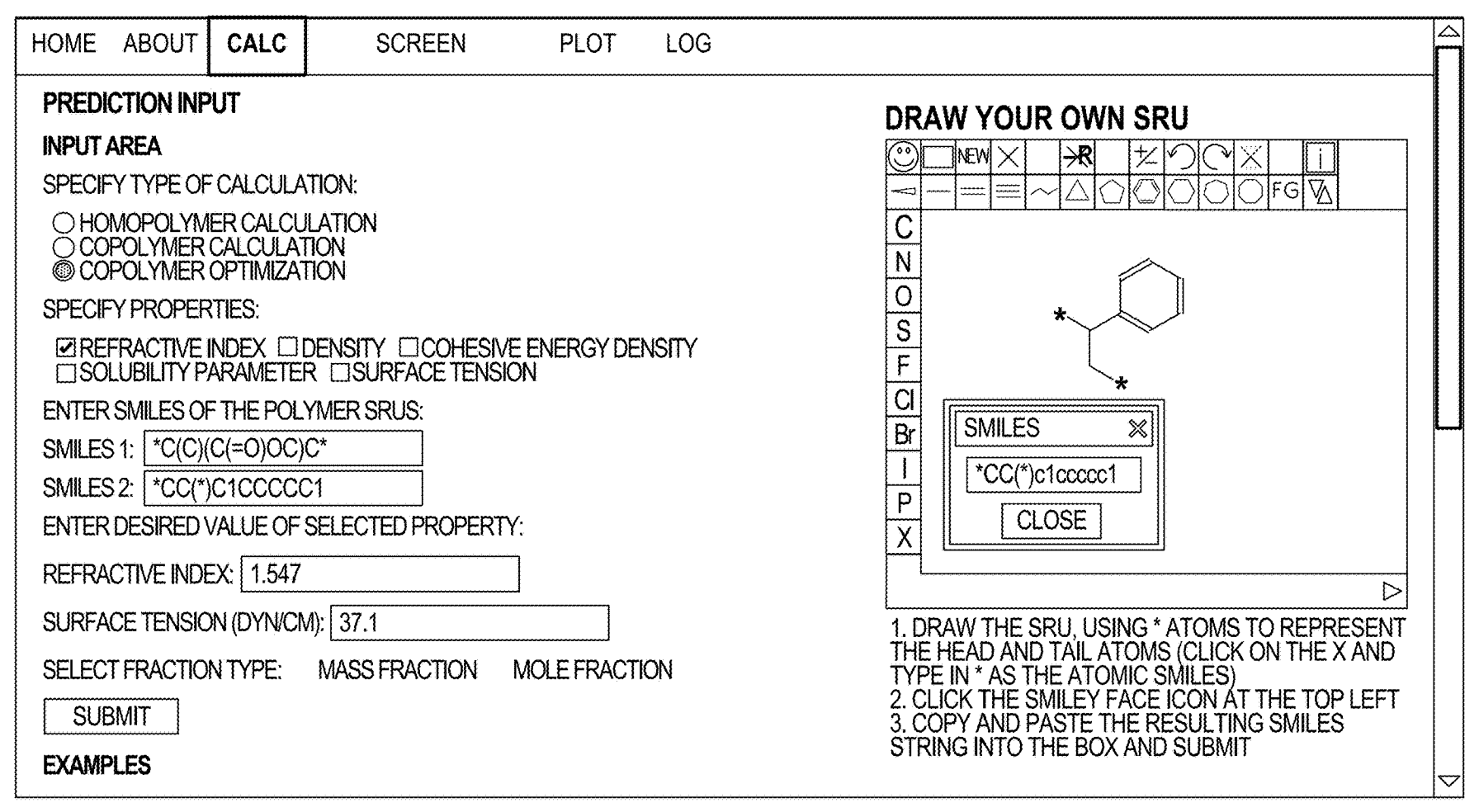

FIGS. 11A-11B illustrate an example user interface for an optimization capability, in accordance with some embodiments.

Figure 12A:
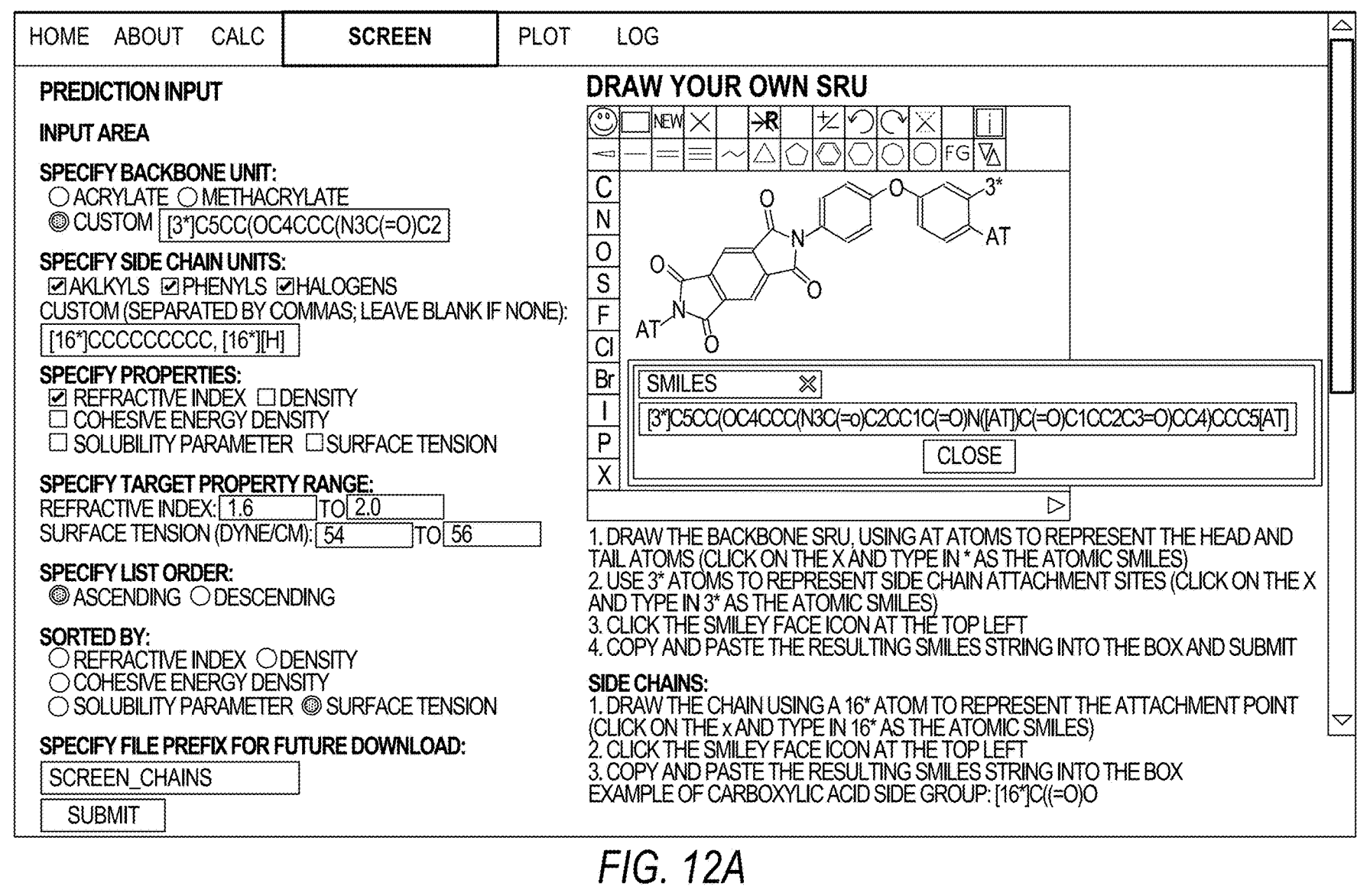
Figure 12B:
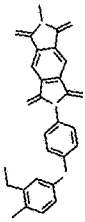

FIGS. 12A-12B illustrate an example user interface for a screening capability, in accordance with some embodiments.

Figure 13:
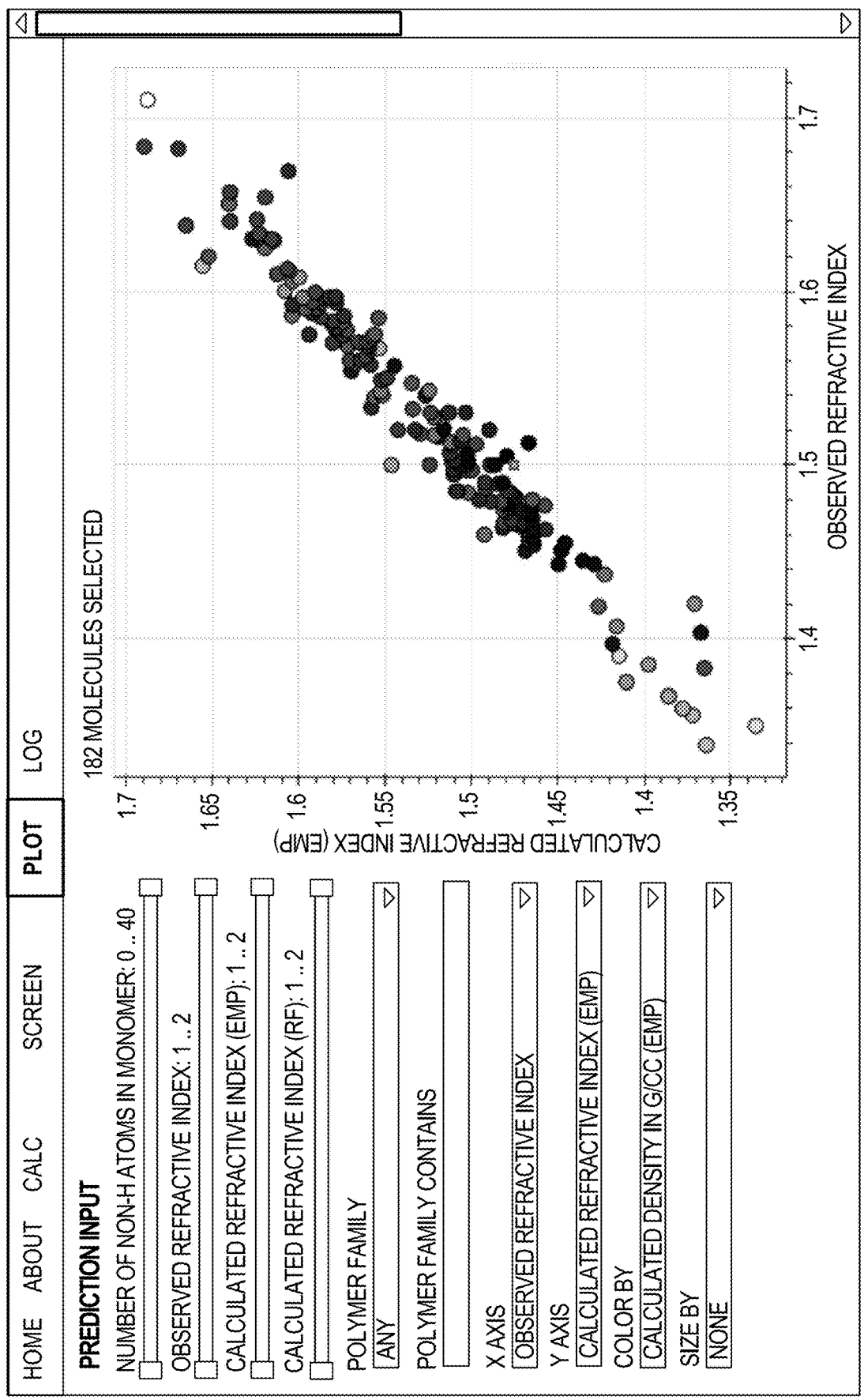
FIG. 13 illustrates an example user interface for a dynamic plot capability, in accordance with some embodiments.

FIG. 13 illustrates an example user interface for a dynamic plot capability, in accordance with some embodiments.

Figure 14A:
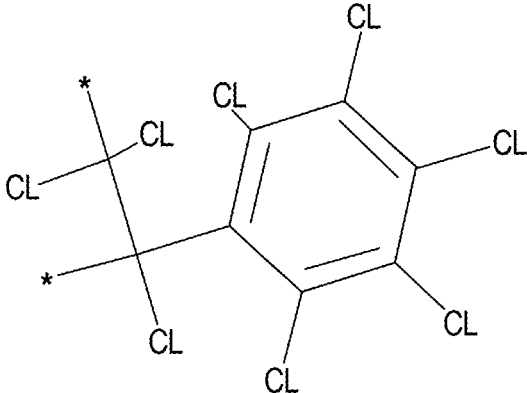
FIG. 14A illustrates an example calculation result, in accordance with some embodiments.

FIG. 14A illustrates an example calculation result, in accordance with some embodiments. FIG. 14A shows a SRU of a polymer to be included in a formulation. FIG. 14A may be displayed in a web portal.

Figure 14B:
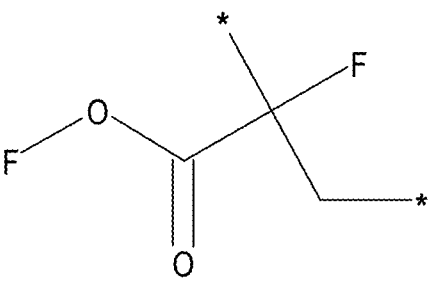
FIG. 14B illustrates an example screening result, in accordance with some embodiments.

FIG. 14B illustrates an example screening result, in accordance with some embodiments. FIG. 14A shows a SRU of a polymer to be blended to reach a target refractive index. FIG. 14B may be displayed in a web portal.

Figure 14C:
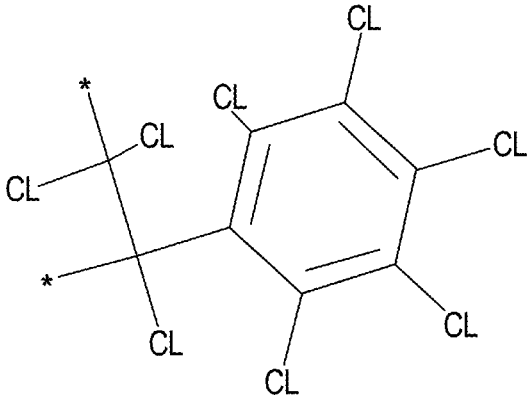
FIG. 14C illustrates an example optimization result, in accordance with some embodiments.

FIG. 14C illustrates an example optimization result, in accordance with some embodiments. FIG. 14C may be displayed in a web portal.

FIGS. 10-14 may be displayed using a graphical user interface (GUI) web portal.

Some aspects are directed to a tool is for accessibility of results for all users, not only those that are familiar with coding. Toward that end, some aspects include a graphic user interface (GUI) web portal. In some cases, the GUI web portal provides the calculation, optimization, screening, and dynamic plot capabilities.

FIGS. 10A-10B show the calculation capability of the web interface. Given an input of SMILES string(s) and a fraction (for a copolymer), the available properties are calculated and results are displayed on the next page. FIG. 10A is the input page, and FIG. 10B is the results page. Currently on the web page, the copolymer calculation is limited to binary systems. In some cases, the user would not be familiar with the SMILES syntax, so some aspects include a chemical structure drawing application on the page. By following the instructions below the application, the user can draw an SRU and obtain its SMILES string to input into the appropriate fields. On the results page, the SRU(s) and other inputs are displayed for the user to check his or her work and then the properties of interest that are calculated are shown below them.

FIGS. 11A-11B shows the optimization capability of the web interface, which is located on the same page as the calculation. The inputs are very similar, except that instead of inputting the fraction, the user can select some target properties. FIG. 11A is the input page, and FIG. 11B is the results page. Currently on the web page, the copolymer optimization is limited to binary systems. The results page looks similar to that of the calculation page; however, now the output comprises the predicted fractions, as well as the calculated values of the properties of interest for those fractions.

FIGS. 12A-12B show the screening capability of the web interface. FIG. 12A is the input page, and FIG. 12B is the results page. Similarly to the calculation page, the SMILES strings can be obtained from the drawing application; however, the instructions are different to accommodate the requirements of the generation algorithm. The input SMILES are categorized as the backbone or the side chains in the appropriate fields. For each property selected, the user specifies a target range to be used as the filter to yield the final set of polymers. Currently on the web page, the screening is limited to the combinatorial generation scheme. The results page displays the final polymer structures and the specified properties in an image format. In addition, a file containing the SMILES strings and properties for each of these candidates is available if the user specifies a file prefix on the input page.

FIG. 13 shows the dynamic plot capability of the web interface. This allows the user to take a look into parts of the database by freely plotting the data with different axes, as well as filtering the data by certain property values or structural families. By giving the user a look into the data, he or she can assess reliability based on the nature of the data that was used to build the models.

In an example use case, a scientist user is considering a polymer (SRU shown in FIG. 14A) to be part of a formulation for a glass coating. The coating is to have a refractive index of 1.440±0.001. This polymer is not well characterized, but is similar to existing polymers in a well-known family. Using the calculation tool, the scientist user can get an idea of what refractive index this polymer would have if used alone for the coating formulation. In this case, a value of 1.654 is obtained. There are two values listed, showing two different models. However, for this particular family of polymers, the empirical model is more robust so that one is used to proceed with further investigation.

The scientist user finds that it does not satisfy the constraints, having a refractive index that is too high, so the scientist user considers using screening to find a space of polymers that have a refractive index below the range. From the chemical cabinet, the scientist user finds a common backbone that varies within a set of side chains. These 225 polymers correspond to an acrylate backbone with some alkyl side groups along with the cyclohexyl, phenyl, and halogen side groups (15 total side chains, 2 attachment sites). These materials do not have well known refractive indices, so the scientist user uses the screening tool to figure out which ones could be the best candidates. This screening process of the 225 polymers takes approximately 20 seconds (e.g., 18-22 seconds) to complete.

Out of these, the scientist user finds only one polymer that would have a low enough refractive index (SRU shown in FIG. 14B), which has a refractive index of 1.420. The scientist user then uses the optimization capability to find a first approximation for the blend composition. Finally, the scientist finds a combination of the mandated polymer with another polymer that can potentially work for his application; with 12.3 wt % of the polymer in FIG. 14A and 87.7 wt % of the polymer in FIG. 14B, the correct refractive index can be attained (FIG. 14C). Instead of testing all of these materials and combinations individually before making a decision, the scientist user has found a solution without wasting material and time.

Some aspects are described below as numbered examples (Example 1, 2, 3, etc.). These numbered examples do not limit the technology disclosed herein.

Example 1 is a method for screening homopolymers, copolymers or blends for fabrication, the method comprising: storing, in a data repository, a plurality of data points, each data point comprising a structural repeating unit (SRU) and at least one material property value for the SRU, wherein each SRU is a homopolymer SRU, a copolymer component SRU or a blend component SRU; determining, using a computing machine, a fingerprint for at least a subset of the SRUs in the data repository; storing, in the data repository, each determined fingerprint in conjunction with a corresponding SRU; generating, using at least a subset of the plurality of data points in the data repository, a quantitative modeling engine to predict material property values, based on SRUs, for homopolymers, copolymers or blends, wherein the quantitative modeling engine is based, at least in part, on the fingerprints; identifying, using the quantitative modeling engine, at least one homopolymer SRU, copolymer SRU set or blend SRU set that has a material property value within a given range, wherein the at least one homopolymer SRU, copolymer component SRU or blend component SRU is selected from a set of SRUs that is different from the SRUs represented by the plurality of data points in the data repository; and providing an output representing the identified at least one homopolymer SRU, copolymer SRU set or blend SRU set.

In Example 2, the subject matter of Example 1 includes, storing, in the data repository, the identified at least one homopolymer SRU, copolymer SRU set or blend SRU set in conjunction with a computed material property value for the identified at least one homopolymer SRU, copolymer SRU set or blend SRU set.

In Example 3, the subject matter of Examples 1-2 includes, wherein the quantitative modeling engine leverages a genetic algorithm, wherein identifying the at least one homopolymer SRU, copolymer SRU set or blend SRU set that has the material property value within the given range comprises: defining, for a test SRU population, attachment sites and side chains; repeating, until all the attachment sites are filled: attaching pseudo-randomly selected side chains to pseudo-randomly selected open attachment sites; identifying, using an objective function for the given material property, a subset of the population having the material property value within the given range; and adding the subset of the population to a result set; upon determining that all the attachment sites are filled: providing an output representing at least a portion of the result set.

In Example 4, the subject matter of Examples 1-3 includes, receiving a copolymer or blend optimization request, the copolymer or blend optimization request comprising: one or more representations of one or more SRUs of the copolymer or blend, at least one material property for optimization, and a target value for each material property for optimization; computing, using at least the quantitative modeling engine, an optimization result comprising at least one copolymer or blend structure wherein, a computed value for each material property for optimization of the at least one copolymer or blend structure is within a threshold percentage of the target value; and providing an output representing the optimization result.

In Example 5, the subject matter of Example 4 includes, wherein the one or more representations of the one or more SRUs of the copolymer or blend comprise one or more SMILES strings, a CAS number or a link to purchase the copolymer or blend.

In Example 6, the subject matter of Examples 4-5 includes, wherein the output representing the optimization result comprises a visual representation of the at least one copolymer or blend structure and the computed value for each material property for optimization.

In Example 7, the subject matter of Examples 4-6 includes, wherein the copolymer or blend optimization request is received, at the computing machine and from a client device, via a graphical user interface (GUI) accessible via an intranet, wherein the GUI is provided for display at the client device.

In Example 8, the subject matter of Examples 1-7 includes, causing fabrication of a homopolymer, copolymer or blend that includes the identified at least one homopolymer SRU, copolymer SRU set or blend SRU set.

In Example 9, the subject matter of Example 8 includes, upon fabrication of the homopolymer, copolymer or blend: receiving, from a user, an experimentally verified material property value; storing, in the data repository, the experimentally verified material property value; and adjusting the quantitative modeling engine based on the experimentally verified material property value.

In Example 10, the subject matter of Example 9 includes, wherein adjusting the quantitative modeling engine comprises: if the experimentally verified material property value is within the given range: increasing a confidence value associated with a computation of the quantitative modeling engine; and if the experimentally verified material property value is not within the given range: modifying the quantitative modeling engine based on the experimentally verified material property value.

In Example 11, the subject matter of Examples 1-10 includes, wherein the quantitative modeling engine leverages one or more of: an artificial intelligence (AI) model, a genetic algorithm, a regression model, a decision tree, a random forest, a neural network, and a combinatorial model.

In Example 12, the subject matter of Examples 1-11 includes, wherein the fingerprint is a chemical or structural fingerprint.

In Example 13, the subject matter of Examples 1-12 includes, wherein the fingerprint is neither a chemical nor a structural fingerprint.

In Example 14, the subject matter of Examples 1-13 includes, if a synthesizing record for a homopolymer, copolymer or blend associated with the at least one homopolymer SRU, copolymer SRU set or blend SRU set is not available: predicting, for the homopolymer, copolymer or blend, an ease of synthesizability.

Example 15 is a system for screening homopolymers, copolymers or blends for fabrication, the system comprising: one or more memory units storing a plurality of data points, each data point comprising a structural repeating unit (SRU) and at least one material property value for the SRU, wherein each SRU is a homopolymer SRU, a copolymer component SRU or a blend component SRU; and processing circuitry in communication with the one or more memory units, the processing circuitry performing operations comprising: determining a fingerprint for at least a subset of the SRUs in the data repository; storing, in the one or more memory units, each determined fingerprint in conjunction with a corresponding SRU; generating, using at least a subset of the plurality of data points in the data repository, a quantitative modeling engine to predict material property values, based on SRUs, for homopolymers, copolymers or blends, wherein the quantitative modeling engine is based, at least in part, on the fingerprints; identifying, using the quantitative modeling engine, at least one homopolymer SRU, copolymer SRU set or blend SRU set that has a material property value within a given range, wherein the at least one homopolymer SRU, copolymer component SRU or blend component SRU is selected from a set of SRUs that is different from the SRUs represented by the plurality of data points in the data repository; and providing an output representing the identified at least one homopolymer SRU, copolymer SRU set or blend SRU set.

In Example 16, the subject matter of Example 15 includes, the operations further comprising: causing fabrication of a homopolymer, copolymer or blend that includes the identified at least one homopolymer SRU, copolymer SRU set or blend SRU set.

In Example 17, the subject matter of Example 16 includes, the operations further comprising: upon fabrication of the homopolymer, copolymer or blend: receiving, from a user, an experimentally verified material property value; storing, in the data repository, the experimentally verified material property value; and adjusting the quantitative modeling engine based on the experimentally verified material property value.

In Example 18, the subject matter of Example 17 includes, wherein adjusting the quantitative modeling engine comprises: if the experimentally verified material property value is within the given range: increasing a confidence value associated with a computation of the quantitative modeling engine; and if the experimentally verified material property value is not within the given range: modifying the quantitative modeling engine based on the experimentally verified material property value.

Example 19 is a machine-readable medium for screening homopolymers, copolymers or blends for fabrication, the machine-readable medium storing instructions which, when executed by a computing machine, cause the computing machine to perform operations comprising: storing, in a data repository, a plurality of data points, each data point comprising a structural repeating unit (SRU) and at least one material property value for the SRU, wherein each SRU is a homopolymer SRU, a copolymer component SRU or a blend component SRU; determining, using the computing machine, a fingerprint for at least a subset of the SRUs in the data repository; storing, in the data repository, each determined fingerprint in conjunction with a corresponding SRU; generating, using at least a subset of the plurality of data points in the data repository, a quantitative modeling engine to predict material property values, based on SRUs, for homopolymers, copolymers or blends, wherein the quantitative modeling engine is based, at least in part, on the fingerprints; identifying, using the quantitative modeling engine, at least one homopolymer SRU, copolymer SRU set or blend SRU set that has a material property value within a given range, wherein the at least one homopolymer SRU, copolymer component SRU or blend component SRU is selected from a set of SRUs that is different from the SRUs represented by the plurality of data points in the data repository; and providing an output representing the identified at least one homopolymer SRU, copolymer SRU set or blend SRU set.

In Example 20, the subject matter of Example 19 includes, the operations further comprising: causing fabrication of a homopolymer, copolymer or blend that includes the identified at least one homopolymer SRU, copolymer SRU set or blend SRU set.

Example 21 is at least one machine-readable medium including instructions that, when executed by processing circuitry, cause the processing circuitry to perform operations to implement of any of Examples 1-20.

Example 22 is an apparatus comprising means to implement of any of Examples 1-20.

Example 23 is a system to implement of any of Examples 1-20.

Example 24 is a method to implement of any of Examples 1-20.

Although an embodiment has been described with reference to specific example embodiments, it will be evident that various modifications and changes may be made to these embodiments without departing from the broader spirit and scope of the present disclosure. Accordingly, the specification and drawings are to be regarded in an illustrative rather than a restrictive sense. The accompanying drawings that form a part hereof show, by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, user equipment (UE), article, composition, formulation, or process that includes elements in addition to those listed after such a term in a claim are still deemed to fall within the scope of that claim.

Moreover, in the following claims, the terms "first," "second," and "third," etc. are used merely as labels, and are not intended to impose numerical requirements on their objects.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A method for screening homopolymers, copolymers or blends for fabrication, the method comprising:
   storing, in a data repository, a plurality of data points, each data point comprising a structural repeating unit (SRU) and at least one material property value for the SRU, wherein each SRU is a homopolymer SRU, a copolymer component SRU or a blend component SRU;
   determining, using a computing machine, a fingerprint for at least a subset of the SRUs in the data repository;
   storing, in the data repository, each determined fingerprint in conjunction with a corresponding SRU;
   generating, using at least a subset of the plurality of data points in the data repository, a quantitative modeling engine to predict material property values, based on SRUs, for homopolymers, copolymers or blends, wherein the quantitative modeling engine is based, at least in part, on the fingerprints;
   identifying, using the quantitative modeling engine, at least one homopolymer SRU, copolymer SRU set or blend SRU set that has a material property value within a given range, wherein the at least one homopolymer SRU, copolymer component SRU or blend component SRU is selected from a set of SRUs that is different from the SRUs represented by the plurality of data points in the data repository;
   providing an output representing the identified at least one homopolymer SRU, copolymer SRU set or blend SRU set;
   causing fabrication of a homopolymer, copolymer or blend that includes the identified at least one homopolymer SRU, copolymer SRU set or blend SRU set;
   upon fabrication of the homopolymer, copolymer or blend: receiving, from a user, an experimentally verified material property value;
   storing, in the data repository, the experimentally verified material property value; and
   adjusting the quantitative modeling engine based on the experimentally verified material property value, wherein adjusting the quantitative modeling engine comprises:
      if the experimentally verified material property value is within the given range: increasing a confidence value associated with a computation of the quantitative modeling engine; and
      if the experimentally verified material property value is not within the given range: modifying the quantitative modeling engine based on the experimentally verified material property value.

2. The method of claim 1, further comprising:
   storing, in the data repository, the identified at least one homopolymer SRU, copolymer SRU set or blend SRU set in conjunction with a computed material property value for the identified at least one homopolymer SRU, copolymer SRU set or blend SRU set.

3. The method of claim 1, wherein the quantitative modeling engine leverages a genetic algorithm, wherein identifying the at least one homopolymer SRU, copolymer SRU set or blend SRU set that has the material property value within the given range comprises:
   defining, for a test SRU population, attachment sites and side chains;
   repeating, until all the attachment sites are filled:
      attaching pseudo-randomly selected side chains to pseudo-randomly selected open attachment sites;
      identifying, using an objective function for the given material property, a subset of the population having the material property value within the given range; and
      adding the subset of the population to a result set;
   upon determining that all the attachment sites are filled: providing an output representing at least a portion of the result set.

4. The method of claim 1, further comprising:
   receiving a copolymer or blend optimization request, the copolymer or blend optimization request comprising: one or more representations of one or more SRUs of the copolymer or blend, at least one material property for optimization, and a target value for each material property for optimization;
   computing, using at least the quantitative modeling engine, an optimization result comprising at least one copolymer or blend structure wherein, a computed value for each material property for optimization of the at least one copolymer or blend structure is within a threshold percentage of the target value; and
   providing an output representing the optimization result.

5. The method of claim 4, wherein the one or more representations of the one or more SRUs of the copolymer or blend comprise one or more SMILES strings, a CAS number or a link to purchase the copolymer or blend.

6. The method of claim 4, wherein the output representing the optimization result comprises a visual representation of the at least one copolymer or blend structure and the computed value for each material property for optimization.

7. The method of claim 4, wherein the copolymer or blend optimization request is received, at the computing machine and from a client device, via a graphical user interface (GUI) accessible via an intranet, wherein the GUI is provided for display at the client device.

8. The method of claim 1, wherein the quantitative modeling engine leverages one or more of: an artificial intelligence (AI) model, a genetic algorithm, a regression model, a decision tree, a random forest, a neural network, and a combinatorial model.

9. The method of claim 1, wherein the fingerprint is a chemical or structural fingerprint.

10. The method of claim 1, wherein the fingerprint is neither a chemical nor a structural fingerprint.

11. The method of claim 1, further comprising:
   if a synthesizing record for a homopolymer, copolymer or blend associated with the at least one homopolymer SRU, copolymer SRU set or blend SRU set is not available: predicting, for the homopolymer, copolymer or blend, an ease of synthesizability.

12. A system for screening homopolymers, copolymers or blends for fabrication, the system comprising:

one or more memory units storing a plurality of data points, each data point comprising a structural repeating unit (SRU) and at least one material property value for the SRU, wherein each SRU is a homopolymer SRU, a copolymer component SRU or a blend component SRU; and processing circuitry in communication with the one or more memory units, the processing circuitry performing operations comprising:

determining a fingerprint for at least a subset of the SRUs in the data repository;

storing, in the one or more memory units, each determined fingerprint in conjunction with a corresponding SRU;

generating, using at least a subset of the plurality of data points in the data repository, a quantitative modeling engine to predict material property values, based on SRUs, for homopolymers, copolymers or blends, wherein the quantitative modeling engine is based, at least in part, on the fingerprints;

identifying, using the quantitative modeling engine, at least one homopolymer SRU, copolymer SRU set or blend SRU set that has a material property value within a given range, wherein the at least one homopolymer SRU, copolymer component SRU or blend component SRU is selected from a set of SRUs that is different from the SRUs represented by the plurality of data points in the data repository;

providing an output representing the identified at least one homopolymer SRU, copolymer SRU set or blend SRU set;

causing fabrication of a homopolymer, copolymer or blend that includes the identified at least one homopolymer SRU, copolymer SRU set or blend SRU set;

upon fabrication of the homopolymer, copolymer or blend: receiving, from a user, an experimentally verified material property value;

storing, in the data repository, the experimentally verified material property value; and adjusting the quantitative modeling engine based on the experimentally verified material property value, wherein adjusting the quantitative modeling engine comprises:

if the experimentally verified material property value is within the given range: increasing a confidence value associated with a computation of the quantitative modeling engine; and if the experimentally verified material property value is not within the given range: modifying the quantitative modeling engine based on the experimentally verified material property value.

13. A non-transitory machine-readable medium for screening homopolymers, copolymers or blends for fabrication, the machine-readable medium storing instructions which, when executed by a computing machine, cause the computing machine to perform operations comprising:

storing, in a data repository, a plurality of data points, each data point comprising a structural repeating unit (SRU) and at least one material property value for the SRU, wherein each SRU is a homopolymer SRU, a copolymer component SRU or a blend component SRU;

determining, using the computing machine, a fingerprint for at least a subset of the SRUs in the data repository;

storing, in the data repository, each determined fingerprint in conjunction with a corresponding SRU;

generating, using at least a subset of the plurality of data points in the data repository, a quantitative modeling engine to predict material property values, based on SRUs, for homopolymers, copolymers or blends, wherein the quantitative modeling engine is based, at least in part, on the fingerprints;

identifying, using the quantitative modeling engine, at least one homopolymer SRU, copolymer SRU set or blend SRU set that has a material property value within a given range, wherein the at least one homopolymer SRU, copolymer component SRU or blend component SRU is selected from a set of SRUs that is different from the SRUs represented by the plurality of data points in the data repository; and providing an output representing the identified at least one homopolymer SRU, copolymer SRU set or blend SRU set;

causing fabrication of a homopolymer, copolymer or blend that includes the identified at least one homopolymer SRU, copolymer SRU set or blend SRU set;

upon fabrication of the homopolymer, copolymer or blend: receiving, from a user, an experimentally verified material property value;

storing, in the data repository, the experimentally verified material property value; and adjusting the quantitative modeling engine based on the experimentally verified material property value, wherein adjusting the quantitative modeling engine comprises:

if the experimentally verified material property value is within the given range: increasing a confidence value associated with a computation of the quantitative modeling engine; and if the experimentally verified material property value is not within the given range: modifying the quantitative modeling engine based on the experimentally verified material property value.

* * * * *

UNITED STATES PATENT AND TRADEMARK OFFICE
CERTIFICATE OF CORRECTION

PATENT NO. : 10,790,045 B1
APPLICATION NO. : 16/653310
DATED : September 29, 2020
INVENTOR(S) : Sushmit Sunil Kumar Goyal et al.

It is certified that error appears in the above-identified patent and that said Letters Patent is hereby corrected as shown below:

On the Title Page

On the page 2, in Column 1, Item (56), Other Publications, Line 4, delete "Applicatio" and insert
-- Application --, therefor.

On the page 2, in Column 2, Item (56), Other Publications, Line 2, delete "Beyong" and insert
-- Beyond --, therefor.

On the page 2, in Column 2, Item (56), Other Publications, Line 6, delete "Informaiton" and insert
-- Information --, therefor.

On the page 2, in Column 2, Item (56), Other Publications, Line 11, delete "Artifical" and insert
-- Artificial --, therefor.

On the page 2, in Column 2, item (56), Other Publications, Line 28, delete "networ" and insert
-- network --, therefor.

Signed and Sealed this
Twenty-seventh Day of September, 2022

Katherine Kelly Vidal
*Director of the United States Patent and Trademark Office*